US005872219A

United States Patent [19]
DiFiore et al.

[11] Patent Number: 5,872,219
[45] Date of Patent: Feb. 16, 1999

[54] ANTIBODIES DRAWN TO THE EPS15 SUBSTRATE FOR EPIDERMAL GROWTH FACTOR RECEPTOR KINASE

[75] Inventors: Pier Paolo DiFiore, Bethesda, Md.; Francesca Fazioli, Ancona, Italy

[73] Assignee: The United States of America, as represented by the Department of Health and Human Services, Washington, D.C.

[21] Appl. No.: 477,389

[22] Filed: Jun. 7, 1995

Related U.S. Application Data

[60] Division of Ser. No. 95,737, Jul. 22, 1993, Pat. No. 5,487,979, which is a continuation-in-part of Ser. No. 935,311, Aug. 25, 1992, Pat. No. 5,378,809.

[51] Int. Cl.$^6$ .......................... C07K 16/18; C07K 16/28; C07K 16/40

[52] U.S. Cl. ................................... 530/387.9; 530/388.2; 530/388.22; 530/388.26; 530/388.85; 530/389.1

[58] Field of Search .............................. 530/387.1, 387.9, 530/388.2, 388.26, 388.85, 389.1

[56] References Cited

U.S. PATENT DOCUMENTS 4,543,439   9/1985   Frackelton .

OTHER PUBLICATIONS

Aaronson, Stuart A., (1991) Growth Factors and Cancer. Science 254:1146–1153.

Bairoch, Amos. (1992). Prosite: a dictionary of sites and patterns in proteins. Nucleic Acids Res. 20:2013–2018.

Bernard, O., et al., (1994) A novel gene, AF–1p. fused to HRX in t(1:11)(p32:q23). is not related to AF–4, AF–9 nor ENL. Oncogene 9:1039–1045.

Coughlin, Shaun R. et al., (1989) Role of phosphatidylinositol kinase in PDGF receptor signal transduction. Science 243:1191–1194.

DiFiore, Pier P. et al., (1987) Overexpression of the human EGF receptor confers an EGF–dependent transformed phenotype to NIH 3T3 cells. Cell 51:1063–1070.

Difiore, Pier P. et al., (1990) The carboxy–terminal domains of erbB–2 and epidermal growth factor receptor exert different regulatory effects on intrinsic receptor tyrosine kinase function and transforming activity. Mol. Cell. Bio. 10:2749–2756.

DiFiore, Pier P. et al., (1990) EGF receptor and erbB–2 tyrosine kinase domains confer cell specificity for mitogenic signaling. Science 248:79–83.

Escobedo, Jaime A. et al., (1991) cDNA cloning of a novel 85 kd protein that has SH2 domains and regulates binding of P13–kinase to the PDGF β–receptor. Cell 65:75–82.

Fazioli, F. et al., (1992) Identification and biochemical characterization of novel putative substrates for the epidermal growth factor receptor kinase*. J. Biol. Chem. 267:5155–5161.

Fazioli, F. et al., (1991) The erbB–2 mitogenic signaling pathway: Tyrosine phosphorylation of phospholipase C–γ and GTPase–activating protein does not correlate with erbB–2 mitogenic potency. Mol. Cell. Biol. 11:2040–2048.

Fazioli, F. et al., (1993) The ezrin–like family of tyrosine kinase substrates: receptor–specific pattern of tyrosine phosphorylation and relationship to malignant transformation. Oncogene 8:1335–1345.

Felgner, P. L. et al. (1991) Gene therapeutics. Nature 349:351–352.

Giard, Donald J. et al., (1973) In vitro cultivation of human tumors: Establishment of cell lines derived from a series of solid tumors. J. Nat'l Cancer Institute 51:1417–1423.

Gould, Kathleen L. et al., (1988) Platelet–derived growth factor induces multisite phosphorylation of $pp60^{c-src}$ and increases its protein–tyrosine kinase activity. Mol. Cell. Bio. 8:3345–3356.

Green, Pamela J. et al., (1986) The role of antisense RNA in gene regulation. Ann. Rev. Biochem. 55:569–597.

Griffin, Linda C. et al., (1989) Recognition of thymine–adenine base pairs by guanine in a pyrimidine triple helix motif. Science 245:967–971.

Heizmann et al., (1991) Intracellular calcium–binding proteins: more sites than insights. Trends Biochem. Sci. 16:98–103.

Helene, C., (1991) The anit–gene strategy: control of gene expression by triplex–forming–oblionucleotides. Anti–Cancer Drug Design 6:569–584.

Hunter, Tony. (1982) Synthetic peptide substrates for a tyrosine protein kinase*. J. Bio. Chem. 257:4843–4848.

Kaplan, David R. et al., (1990) PDGF β–receptor stimulates tyrosine phosphorylation of GAP and association of GAP with a signaling complex. Cell 61:125–133.

Kazlauskas, Andrius et al., (1989) Autophosphorylation of the PDGF receptor in the kinase insert region regulates interactions with cell proteins. Cell 58:1121–1133.

Kazlauskas, Andrius et al., (1990) Binding of GAP to activated PDGF receptors. Science 247:1578–1581.

Kirkness, Ewen F. et al., (1991) Isolation, characterization, and localization of human genomic DNA encoding the β1 subunit of the $GABA_A$ receptor (GABRB1). Genomics 10:985–995.

Koch, C. Anne et al., (1991) SH2 and SH3 domains: Elements that control interactions of cytoplasmic signaling proteins. Science 252:668–674.

Koerner, T.J. et al., (1991) High–expression vectors with multiple cloning sites for constructin of trpE fusion genes: pATH vectors. Methods Enzymol. 194:477–490.

(List continued on next page.)

*Primary Examiner*—Toni R. Scheiner
*Assistant Examiner*—Nancy A. Johnson
*Attorney, Agent, or Firm*—Knobbe, Martens, Olson & Bear, LLP

[57] ABSTRACT

A new substrate of epidermal growth factor receptor and certain other tyrosine kinase receptors denominated eps15, polynucleotides encoding eps15, antisense eps15 polynucleotide, triple helix eps15 polynucleotide, antibodies to eps15, and assays for determining eps15.

11 Claims, 3 Drawing Sheets

OTHER PUBLICATIONS

Kozak, Marilyn, (1989) The scanning model for translation: An update. J. Cell. Biol. 108:229–241.

Kraus, M.H. et al., (1991). Detection and isolation of novel protein–tyrosine kinase genes employing reduced stringency hybridization. Methods Enzymol. 200:546–556.

Kypta, Robert M. et al., (1990) Association between the PDGF receptor and members of the src family of tyrosine kinases. Cell 62:481–492.

Lee, James et al., (1989) HER2 cytoplasmic domain generates normal mitogenic and transforming signals in a chimeric receptor. EMBO J 8:167–173.

Lehvaslaiho, Heikki et al., (1989) A chimeric EGF–R—neu proto–oncogene allows EGF to regulate neu tyrosine kinase and cell tranformation. EMBO J. 8–159–166.

Lonardo, Fulvio et al., (1990) The normal erbB–2 product is an atypical receptor–like tyrosine kinase with constitutive activity in the absence of ligand. New Biol. 2:992–1003.

Margolis, B. et al., (1989) EGF induces tyrosine phosphorylation of phospholipase C–II: A potential mechanism for EGF receptor signaling. Cell 57:1101–1107.

McCombie, W. Richard et al., (1991) The use of exonuclease III deletions in automated DNA sequencing. Methods 3:33–40.

McLachlan, Andrew D. et al., (1983) Periodic features in the amino acid sequence of nematode myosin rod. J. Mol. Bio. 164:605–626.

Meisenhelder, Jill et al., (1989) Phospholipase C–$\gamma$ is a substrate for the PDGF and EGF receptor protein–tyrosine kinases in vivo and in vitro. Cell 57:1109–1122.

Molloy, Christopher J. et al., (1989) PDGF induction of tyrosine phosphorylation of GTPase activating protein. Nature 342:711–713.

Morrison, Deborah K. et al., (1988) Direct activation of the serine/threonine kinase activity of Raf–1 through tyrosine phosphorylation by the PDGF $\beta$–receptor. Cell 58:649:657.

Morrison, Deborah K. et al., (1989) Signal transduction from membrane to cytoplasm: Growth factors and membrane–bound oncogene products increase Raf–1 phosphorylation and associated protein kinase activity. Proc. Natl. Acad. Sco. USA 85:8855–8859.

Otsu, Masayuki et al., (1991) Characterization of two 85 kd proteins that associate with receptor tyrosine kinases, middle–T/pp60$^{c-src}$ complexes and P13 kinase. Cell 65:91–104.

Rossi, John J. et al., (1991) The potential use of catalytic RNAs in therapy of HIV infection and other diseases. Pharm. Ther. 50:245–254.

Ruderman, Neil B. et al., (1990) Activation of phosphatidylinositol 3–kinase by insulin. Proc. Natl. Acad. Sci. USA 87:1411–1415.

Segatto, Oreste et al., (1991) The juxtamembrane regions of the epidermal growth factor receptor and gp185$^{erbB-2}$ determine the specificity of signal transduction. Mol. Cell. Biol. 11:3191–3202.

Skolnik, E.Y. et al., (1991) Cloning of P13 kinase—Associated p85 utilizing a novel method for expression/cloning of target proteins for receptor tyrosine kinases. Cell 65:83–90.

Ullrich, Axel et al., (1990) Signal transduction by receptors with tyrosine kinase activity. Cell 61:203–212.

Varticovski, Lyuba et al., (1989) The colony stimulating factor–1 receptor associates with and activates phosphatidylinositol–3 kinase. Nature 342:699–702.

Wahl, Matthew I. et al., (1989) Platelet–derived growth factor induces rapid and sustained tyrosine phosphorylation of phospholipase c–$\gamma$ in quiescent BALB/c 3T3 cells. Mol. Cell. Biol. 9:2934–2943.

Wolff, Jon A. et al., (1990) Direct gene transfer into mouse muscle in vivo. Science 247:1465–1468.

Wong, William et al., (1994) The human eps15 gene, encoding a tyrosine kinase substrate, is conserved in evolution and maps to 1p31–p32. Oncogene 9:1591–1597.

Fazioli, F., et al., (1993) eps15, A Novel Tyrosine Kinase Substrate, Exhibits Transforming Activity, Molecular Cellular Biology 13:5814–5828.

ANTIBODIES DRAWN TO THE EPS15 SUBSTRATE FOR EPIDERMAL GROWTH FACTOR RECEPTOR KINASE

CROSS REFERENCE TO RELATED APPLICATIONS

This application is a divisional of U.S. patent application Ser. No. 08/095,737, filed Jul. 22, 1993, now U.S. Pat. No. 5,487,979 which is a continuation in part of Ser. No. 07/935,311, filed Aug. 25, 1992, now U.S. Pat. No. 5,378,809, which applications are hereby incorporated by reference herein.

FIELD OF THE INVENTION

The present invention relates to substrates for the epidermal growth factor receptor kinase, polynucleotides encoding the substrates, and methods for using the substrates.

BACKGROUND OF THE INVENTION

The cellular machinery involved in mitogenesis is complex, and not fully understood. In general, receptors present on the cell surface bind growth factors, resulting in an activated receptor. In particular, the receptors of interest are endowed with intrinsic tyrosine kinase activity, and are known as tyrosine kinase receptors or TKRs. The activated receptors, in turn, phosphorylate intracellular substrates. These phosphorylated substrates are responsible for a series of events that leads to cell division. This process is generally referred to as "mitogenic signal transduction." The molecular machinery involved in this process is considered to be the "mitogenic signaling pathway."

Growth factors and hormones exert pleiotropic effects on cellular functions, including mitogenic stimulation and modulation of differentiation and metabolism (Ullrich et al., *Cell* 61:203–212 (1990); Aaronson, *Science* 254:1146–1153 (1991)). In many cases, these effects are mediated by the interaction of growth factors with cell surface tyrosine kinase receptors (TKRs), resulting in enhanced receptor catalytic activity and tyrosine phosphorylation of intracellular substrates (Ullrich et al., supra; Aaronson, supra). Data regarding the nature of these second messenger systems is still scanty, although some molecules which associate and/or are tyrosine phosphorylated by TKRs have been identified. These include the γ isozyme of phospholipase C (PLC-γ) (Margolis et al., *Cell* 57:1101–1107 (1989); Meisenhelder et al., *Cell* 57:1109–1122 (1989); Wahl et al., *Mol. Cell. Biol.* 9:2934–2943 (1989)); the p21ras GTPase activating protein (GAP) (Molloy et al., *Nature* 342:711–714 (1989); Kaplan et al., *Cell* 61:125–133 (1990); Kazlauskas et al., *Science* 247:1578–1581 (1990)); the raf serine-threonine kinase (Morrison et al., *Proc. Natl. Acad. Sci. USA* 85:8855–8859 (1988); Morrison et al., *Cell* 58:649–657 (1989)); the p85 subunit of the phosphatidylinositol 3-kinase (PtdIns-3K); (Coughlin et al., *Science* 243:1191–1194 (1989); Kazlauskas et al., *Cell* 58:1121–1133 (1989); Varticovski et al., *Nature* 342:699–702 (1989); Ruderman et al., *Proc. Natl. Acad. Sci. USA* 87:1411–1415 (1990); Escobedo et al., *Cell* 65:75–82 (1991); Skolnik et al., *Cell* 65:83–90 (1991); Otsu et al., *Cell* 65:91–104 (1991)) and some cytoplasmic tyrosine kinases (Gould et al., *Mol. Cell. Biol.* 8:3345–3356 (1988); Kypta et al., *Cell* 62:481–492 (1990)). These signaling molecules are thought to mediate at least in part the mitogenic effects of TKRs (Ullrich et al., *Cell* 61:203–212 (1990); Aaronson, *Science* 254:1146–1153 (1991)).

However, the epidermal growth factor (EGF) receptor (EGFR) does not appear to efficiently interact with known second messenger systems (Fazioli et al., *Mol. Cell. Biol.* 11:2040–2048 (1991); Segatto et al., *Mol. Cell. Biol.* 11:3191–3202 (1991)). Thus, there is a need to ascertain the mechanism by which the EGFR functions in mitogenesis, and a particular need to identify and characterize the substrate (if any) of the EGFR.

Errors which occur in the mitogenic signaling pathway, such as alterations in one or more elements of that pathway, are implicated in malignant transformation and cancer. It is believed that in at least some malignancies, interference with abnormal mitogenic signal transduction could cause reversion of cells to a normal phenotype.

In addition, reagents useful in identifying molecular components of the mitogenic signaling pathway would find utility as tumor markers for therapeutic, diagnostic, and prognostic purposes. Furthermore, identification of how such components differ from normal components in malignant tissue might be of significant value in understanding and treating such malignancies. Alterations of the EGFR mitogenic signal transduction pathway have been described in several human tumors. Accordingly, substrates of the EGFR are of particular interest.

Finally, there is a need to identify reagents that can be used to determine the tyrosine kinase activity of particular samples of biological origin. Determination of the tyrosine kinase activity of samples could have value in the therapy, diagnosis, and prognosis of neoplasia and other disorders connected with abnormal mitogenic signaling pathways.

It is therefore an object of the present invention to provide reagents and methods useful in identifying components of the mitogenic signal transduction pathway, for determining tyrosine kinase activity of samples, and for determining how particular components of the pathway in abnormal tissue differ from normal components. In particular, it is an object of the invention to provide reagents and methods that relate to the EGFR substrate(s).

SUMMARY OF THE INVENTION

A method is disclosed which allows direct cloning of intracellular substrates for tyrosine kinase receptors (TKRs). By applying this technique to the study of the epidermal growth factor (EGF) receptor (EGFR) signaling pathway, a cDNA designated eps15 has been isolated. The structural features of the deduced eps15 gene product allow its subdivision into three domains. Domain I contains signatures of a regulatory domain, including a candidate tyrosine phosphorylation site and EF-hand type calcium-binding domains. Domain II presents the characteristic heptad repeats of coiled-coil rod-like proteins. Domain III displays a repeated aspartic acid-proline-phenylalanine motif reminiscent of a consensus sequence of several methylases. Eps15 does not bear the Src homology 2 (SH2) and Src homology 3 (SH3) domains, characteristic signatures of TKR substrates. Antibodies specific to the eps15 gene product recognize a protein of 142 kDa and a minor component of 155 kDa, which are phosphorylated on tyrosine following EGFR activation by EGF in vivo. In addition, phosphorylation of the eps15 gene product must be relatively receptor-specific, since erbB-2, an EGFR-related kinase, phosphorylates it very inefficiently. By employing chimeric molecules between EGFR and gp185$^{erbB-2}$, the region of the EGFR responsible for the differential phosphorylation of eps15 could be mapped to its juxtamembrane region. Overexpression of eps15 is sufficient to transform NIH-3T3 cells, thus implicating the eps15 gene product in the regulation of mitogenic signals.

Thus, one aspect of the present invention is isolated or purified polynucleotide encoding eps15 substrate of the epidermal growth factor receptor, preferably mammalian eps15, and more preferably human eps15. The sequence can include polynucleotide coding for mouse eps15, including polynucleotide encoding the amino acid sequence of SEQ ID NO:4, the DNA sequence of SEQ ID NO:3, and a mRNA transcript of SEQ ID NO:3. Also encompassed within the scope of the invention is sequence coding for human eps15 that includes the polynucleotide encoding the amino acid sequence of SEQ ID NO:2, the DNA sequence of SEQ ID NO:1, and a mRNA transcript of SEQ ID NO:1. Moreover, the invention includes an antisense oligonucleotide and a triple helix probe capable of blocking expression of the eps15 gene product, preferably including at least 15 nucleotides.

The invention further comprises isolated or purified eps15, preferably mammalian eps15, and more preferably human eps15. Included within the scope of the invention is mouse eps15, which can have the amino acid sequence of SEQ ID NO:4. The human eps15 advantageously includes the amino acid sequence of SEQ ID NO:2. The concentration of the isolated or purified eps15 is preferably at least 1 μg/ml.

Another aspect of the invention is isolated or purified antibody to eps15, including both monoclonal and polyclonal antibody.

Yet another aspect of the invention is a construct including a vector and sequence encoding the eps15 substrate; and a host transformed therewith.

Furthermore, the invention features a method for enhancing the mitogenic response of cells to mitogenic factors, including the step of administering to the cells an effective mitogenic-response enhancing amount of eps15.

Another aspect of the invention is a method for determining TKR tyrosine kinase activity in a biological sample, including the steps of combining eps15 with the sample, and measuring tyrosine phosphorylation of the eps15 by the TKR tyrosine kinase in the sample.

The invention also provides a method for determining epsis in a sample, including the steps of contacting the sample with antibody to eps15, such that an immunological complex forms between eps15 and the antibody, and detecting the formation of the immunological complex.

DETAILED DESCRIPTION OF THE INVENTION

Figure 1:
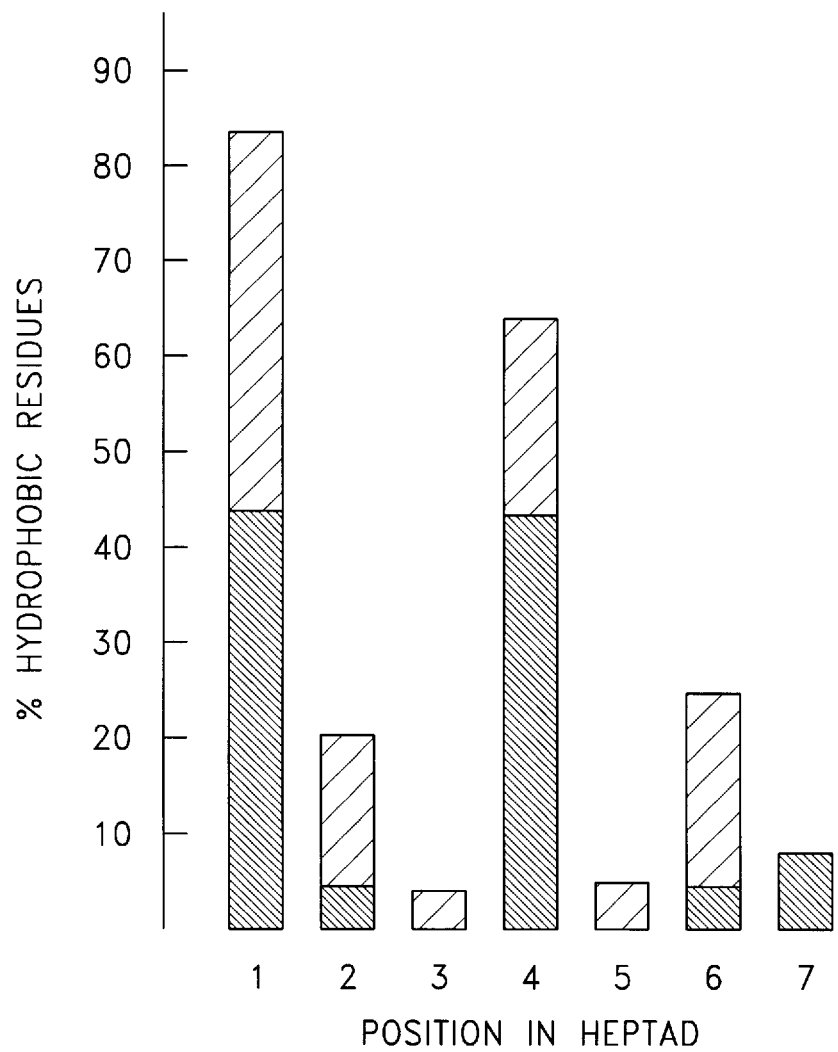
FIG. 1 presents an analysis of the heptads in the second of the three structural domains charaterizing eps15 deduced from the the mouse CDNA. The amino acid position in each heptad is plotted against the frequency of hydrophobic residues at each position. Hydrophobicity was evaluated according to Kyte and Doolittle. (Kyte and Doolittle, *J. Mol. Biol.* 157:105–132 (1982)). Leucine residues are represented by closed boxes, other hydrophobic residues by dashed boxes.

The present invention includes the discovery of a novel epidermal growth factor (EGF) receptor (EGFR) substrate which is called eps15 (EGFR pathway substrate), together with complete cDNA and deduced protein sequences for the murine eps15 (SEQ ID NOS:3 and 4, respectively) and cDNA and deduced protein sequences for the human eps15 (SEQ ID NOS:1 and 2, respectively). The protein sequences are referred to as "deduced" sequences simply because they were determined from the nucleotide sequence, rather than from analysis of purified natural protein.

In addition, the present invention provides methodology for isolating cDNA and protein sequences of other species; antibodies which recognize the proteins encoded by the cDNAs; expression vectors for producing eps15 in prokaryotic or eukaryotic cells; cell lines expressing eps15; and assays using the antibodies, cDNA sequences, and proteins.

The sequences falling within the scope of the present invention are not limited to the specific sequences described, but include functional fragments thereof, that is, fragments that function in substantially the same way as do the specific sequences described. Functional polynucleotide fragments having at least about 60 nucleotides, advantageously at least about 30 nucleotides, and preferably at least about 15 nucleotides are contemplated. Regarding functional polypeptide fragments, those having at least about 20 amino acid residues, advantageously at least about 10 amino acid residues, and preferably at least about 5 amino acid residues are considered. Moreover, the invention includes conservative variants of the specific proteins described, ie., substituents incorporating conservative changes for any of the amino acid residues provided herein. Further, to accommodate codon degeneracy, the invention encompasses any DNA sequence encoding the proteins of the present invention.

The eps15 proteins, polynucleotide sequences, constructs, vectors, clones, and other materials comprising the present invention can advantageously be in isolated form. As used herein, the term "isolated" denotes that the material has been removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated.

It is also advantageous that the sequences and other materials comprising the invention be in purified form. The term "purified" does not require absolute purity; rather, it is intended as a relative definition. Purification of starting material or natural material means that the concentration of the material is at least about 2, 5, 10, 100 or 1000 times its original concentration (for example), advantageously 0.01% by weight, preferably at least about 0.1% by weight. Purified preparations of about 0.5%, 1%, 5%, 10% and 20% by weight are also contemplated.

A. Overview

Two lines of evidence indicate that the EGF receptor is not very efficient at coupling with known second messenger systems. There is a low stoichiometry of tyrosine phosphorylation (~1% of the total pools), of PLC-γ, and GAP weak induction of PIP2 breakdown, and very little phosphorylation/activation of raf or activation of PtdIns-3K by EGFR, even when overexpressed at levels of approximately $2 \times 10^6$ receptors/cell (Fazioli et al., *Mol. Cell Biol.* 11:2040–2048 (1991)). In addition, a mitogenesisincompetent mutant of the EGFR (EGFR A660–667 Segatto et al., *Mol. Cell Biol.* 11:3191–3202 (1991)) did not show any decreased ability to phosphorylate PLC-γ or GAP, or to induce PIP2 breakdown as compared to the wild type EGFR (Segatto et al., *Mol. Cell Biol.* 11:3191–3202 (1991)). This strongly indicated the existence of alternative effector pathways for mitogenic signal transduction by EGFR.

Characterization of EGFR-activated pathways requires the identification of novel proteins that are tyrosine phosphorylated following stimulation of this receptor kinase. The present invention utilized a novel approach to the cloning of cDNAs coding for EGFR substrates, as disclosed in Fazioli et al., *J. Biol. Chem.* 267:5155–5157 (1992) and Fazioli et al., *Oncogene* 8:1335–1345 (1993), which are hereby incorporated by reference. The approach relies on batch purification of the entire set of proteins that are phosphorylated on tyrosine following EGFR activation and generation of antisera directed against the entire pool of purified proteins. These sera can be used to immunologically characterize various substrates or for expression screening of CDNA libraries.

B. Identification of Murine CDNA Encoding eps15

Antibodies to phosphotyrosine were used to isolate proteins that were tyrosine-phosphorylated upon EGF stimulation of NIH-3T3 murine fibroblasts overexpressing the EGFR (NIH-EGFR cells) as discussed in Example 1. A strategy was developed that allowed direct cloning of the cDNAs encoding several of these proteins. Briefly, two polyclonal sera were generated using the entire purified pool of phosphotyrosine (pTyr)-containing proteins as an immunogen (Fazioli et al., *J. Biol. Chem.* 267:5155–5157 (1992)). These antibodies were used for expression screening of CDNA libraries, as reported in greater detail in Examples 1 and 2.

A novel cDNA isolated by this method was sequenced as described in Example 3, and the encoded protein was designated eps15. The nucleotide sequence of the eps15 cDNA is presented herein as SEQ ID NO:3. The deduced amino acid sequence, given herein as SEQ ID NO:4, describes a protein bearing a candidate tyrosine phosphorylation site but, surprisingly, no Src homology 2 (SH2) or Src homology 3 (SH3) domains which are the characteristic hallmarks of TKR substrates. Antibodies generated against the cDNA protein product in accordance with Example 4 recognized in NIH-EGFR cells a 142 kDa protein and a less abundant 155 kDa protein, both of which were phosphorylated on tyrosine residues following treatment of intact cells with EGF.

C. Features and Properties of eps15 Protein

The amino acid sequence deduced from the single eps15 ORF provides a 897 amino acid protein with a calculated molecular weight of approximately 98 kDa.

The features of the deduced polypeptide indicated the presence of three structural domains. Domain I (spanning between amino acid positions 9–314) consisted of three imperfect repeats of 95–97 amino acids, with a 55–60% overall degree of conservation. The second repeat included a tyrosine, at position 132, flanked by the consensus sequence for putative tyrosine phosphorylation sites (Bairoch, *Nucleic Acids. Res.* 20:2013–2018 (1992); Hunter, *J. Biol. Chem.* 257:4843–4848 (1982)). This tyrosine residue was conserved in the first and third repeat of Domain I, although it was not flanked by the phosphorylation consensus. The second and third repeat also contained consensus sequences for calcium-binding domains of the EF-hand type (Bairoch, *Nucleic Acids. Res.* 20:2013–2018 (1992); Heizmann et al., *Trends Biochem. Sci.* 16:98–103 (1991)) at positions 173–185 and 236–248, respectively.

Figure 2:
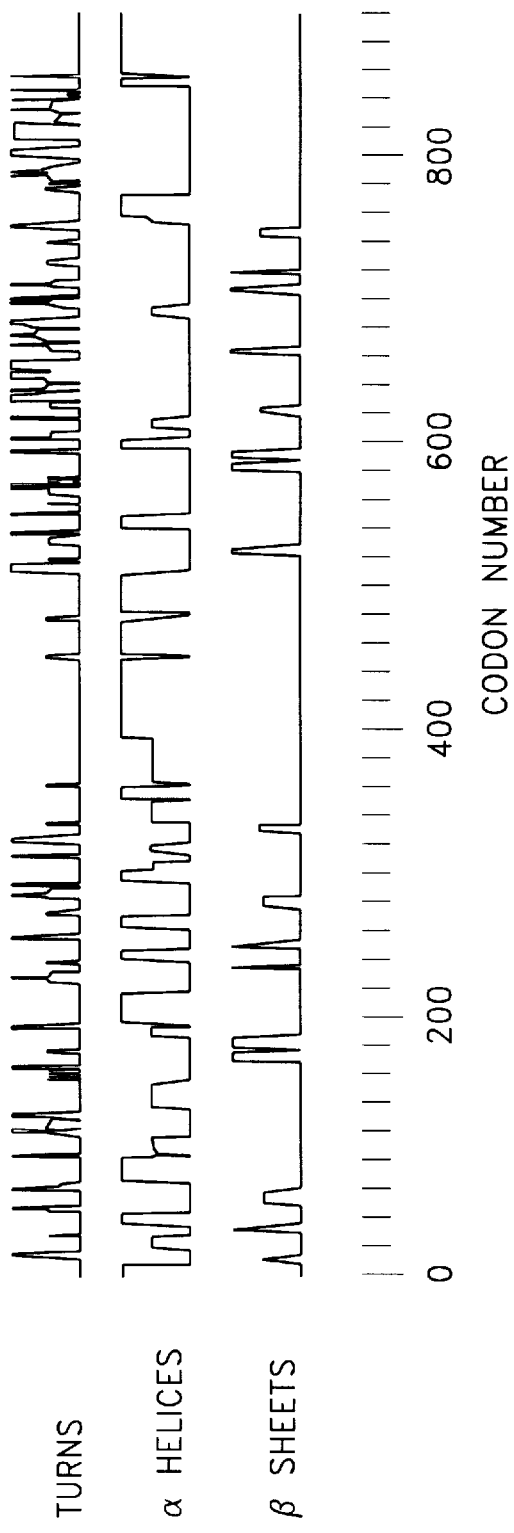
FIG. 2 provides a secondary structure analysis of the eps15 protein product deduced from the mouse cDNA. Scores were calculated with the Chou-Fassman algorithm. (Chou and Fassman, *Adv. Enzymol. Relat. Areas Mol. Biol.* 47:45–148 (1978)). Turns, alpha helices, and beta sheets are graphed against amino acid number.

Domain II (amino acid positions 335–502) presented the typical features of an α-helical coiled-coil structure, common to several cytoskeleton-related proteins. The requisite for the formation of a coiled-coil α-helix is the presence of heptad repeats, in which the first and fourth positions usually contain hydrophobic amino acid residues (McLachlan et al., *J. Mol. Biol.* 164:605–626 (1983)). Domain II of eps15 was composed of 24 contiguous heptads whose positions 1 and 4 were markedly biased in favor of apolar amino acids, in particular leucine. FIG. 1. In addition, Domain II contained only 2 glycines and 1 proline (1.8% of the total residues, as opposed to 11.8% in the entire eps15) which are both strong α-helix breakers. Secondary structure analysis (FIG. 2) indicated that this region has the potential to form an α-helix.

Figure 3:
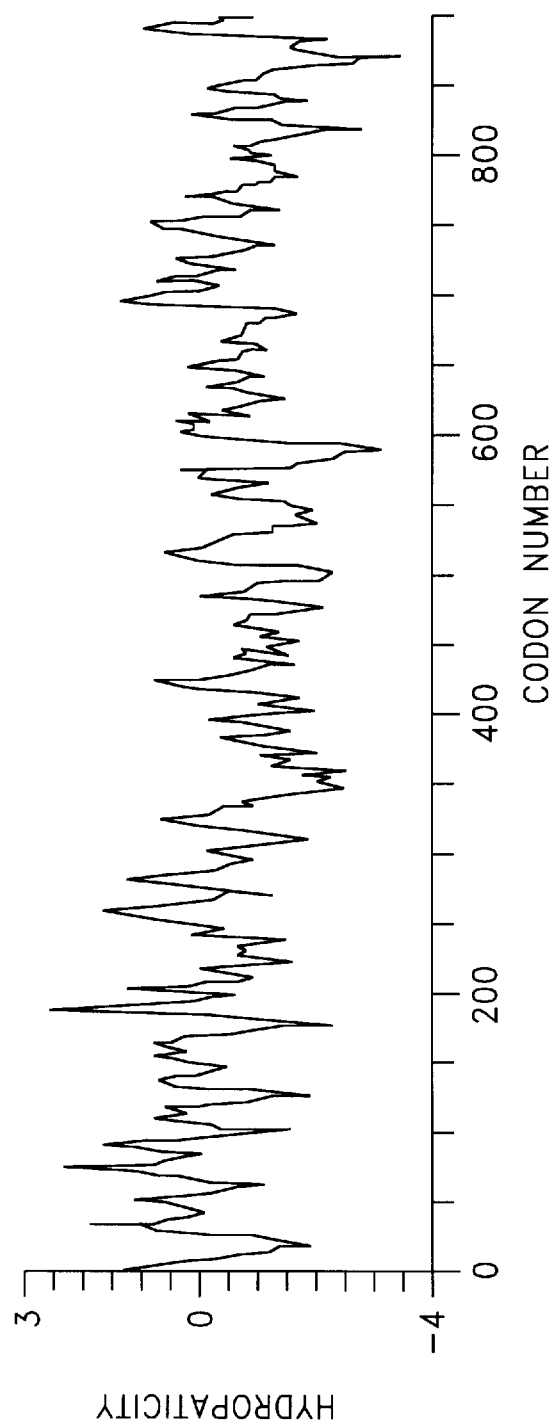
FIG. 3 profiles the hydropaticity of eps15 deduced from the mouse cDNA. Values were calculated according to Kyte and Doolittle (Kyte and Doolittle, supra) on a window of 10 amino acids with equal weights. Positive values indicate hydrophobicity, negative values hydrophilicity. Hydropaticity is diagrammed against amino acid number.

Domain III (amino acids 598–842) was characterized by the repetition of a three amino acid motif, aspartic acidproline-phenylalanine (DPF repeat); thirteen perfect DPFs and eight imperfect repeats (DXF, DPX and XPF) were identified. A hydropaticity plot of eps15 (FIG. 3) did not reveal any long stretch of hydrophobic amino acids that would qualify as a transmembrane domain, nor any signal peptide.

Remarkably, no Src homology 2 (SH2) or Src homology 3 (SH3) domains, which are characteristic signatures of TKR substrates (Koch et al., *Science* 252:668–674 (1991)), were identifiable. Src homology (SH) regions 2 and 3 are noncatalytic regions conserved among substrates regulated by TKRs. The SH2 domains of these substrates bind activated TKRs and other tyrosine phosphorylated proteins, thus suggesting a role for SH2 in the mediation of protein-protein interactions. SH3 sequences are implicated in acting together with SH2 to modulate interactions with the cytoskeleton and membrane. The lack of SH2 and SH3 domains suggests that eps15 exploits other novel mechanisms for regulating protein-protein interactions during signal transduction.

D. Obtaining of Human CDNA for eps15

The present invention includes partial and complete human cDNA sequences and human genomic DNA sequences for eps15. A partial human eps15 sequence was obtained by PCR amplification from a human cDNA library using short sequences of the mouse eps15 cDNA as primers. This procedure is explained in more detail in Example 5.

A resultant PCR product containing partial sequence for human eps15 was used as a probe to identify a human cDNA clone potentially corresponding to a full-length transcript. See Example 6. The cDNA sequence for this human eps15 clone is set forth herein as SEQ ID NO:1. The deduced protein sequence of the human eps15 was 896 amino acids in length and included the entire open reading frame corresponding to the mouse eps15 cDNA. The human amino acid sequence displayed 90% identity to the mouse sequence. The peptide sequence for human eps15 is included herein as SEQ ID NO:2.

Although the described human eps15 CDNA clone may not be full length, such a clone can be obtained using well known methodology. For example, antibodies against the expression product of the human CDNA sequence of SEQ ID NO:1 can be used for expression screening of a cDNA library. These experiments can employ the techniques set forth in Example 4 to generate polyclonal antibodies against human eps15, and then candidate clones can be identified as set forth in Example 2 and characterized by sequencing as set forth in Example 3.

Additionally, conventional biochemical techniques permit use of a partial or complete cDNA clone as a probe to identify a cDNA corresponding to a full-length transcript or a genomic clone having the complete eps15 gene, including regulatory and promoter regions, exons, and introns.

One general approach for obtaining a complete cDNA sequence or genomic DNA sequence corresponding to the human eps15 gene is as follows:

1. Label a human eps15 cDNA and use it as a probe to screen a human lambda phage cDNA library or a human plasmid cDNA library.

2. Identify colonies containing clones related to the probe cDNA and purify them by known purification methods.

3. Nucleotide sequence the ends of the newly purified clones to identify full length sequences.

4. Perform complete nucleotide sequencing of putative full length clones by Exonuclease III digestion or primer walking using art-known means. Northern blots of mRNA from various tissues using at least part of the clone as a probe can be performed to check the size of the mRNA against that of the purported full length cDNA.

More particularly, all or part of the DNA sequence of SEQ ID NO:1 may be used as a probe to identify cDNA clones containing the full length CDNA sequence. The partial sequence of SEQ.ID NO:1, or portions thereof, can be nick-translated or end-labelled with $^{32}P$ using polynucleotide kinase and labelling methods known to those with skill in the art (*Basic Methods in Molecular Biology,* L. G. Davis, M. D. Dibner, and J. F. Battey, ed., Elsevier Press, NY 1986). A lambda library can be directly screened with the labelled CDNA probe, or the library can be converted en masse to pBluescript® (Stratagene, La Jolla, Calif.) to facilitate bacterial colony screening. Both methods are well known in the art.

Briefly, filters with bacterial colonies containing the library in pBluescript® or bacterial lawns containing lambda plaques are denatured and the DNA is fixed to the filters. The filters are hybridized with the labelled probe using hybridization conditions described by Davis et al. All or part of SEQ ID NO:1, cloned into lambda or pBluescript®, can be used as a positive control to assess background binding and to adjust the hybridization and washing stringencies necessary for accurate clone identification. The resulting autoradiograms are compared to duplicate plates of colonies or plaques, where each exposed spot corresponds to a positive colony or plaque. The colonies or plaques are selected, expanded, and the DNA is isolated from the colonies for further analysis and sequencing.

Positive cDNA clones in phage lambda may be analyzed to determine the amount of additional sequence they contain using PCR with one primer from the sequence obtained from SEQ ID NO:1 and the other primer from the vector. Clones with a larger vector-insert PCR product than the original clone are analyzed by restriction digestion and DNA sequencing to determine whether they contain an insert of the same size or similar as the mRNA size on a Northern blot.

Once one or more overlapping cDNA clones are identified, the complete sequence of the clones can be determined. The preferred method is to use Exonuclease III digestion (McCombie et al., *Methods* 3:33–40 (1991)). A series of deletion clones is generated, each of which is sequenced. The resulting overlapping sequences are assembled into a single contiguous sequence of high redundancy (usually three to five overlapping sequences at each nucleotide position), resulting in a highly accurate final sequence.

A similar screening and clone selection approach can be applied to obtaining cosmid or lambda clones from a genomic DNA library (Kirkness et al., *Genomics* 10:985–995 (1991)). Although the process is much more laborious, these genomic clones can also be sequenced in their entirety. A shotgun approach is preferred to sequencing clones with inserts longer than 10 kb (genomic cosmid and lambda clones). In shotgun sequencing, the clone is randomly broken into many small pieces, each of which is partially sequenced. The sequence fragments are then aligned via computer to produce a final contiguous sequence with high redundancy. An intermediate approach to obtaining genomic DNA sequence is to sequence just the promoter region and the intron-exon boundaries and to estimate the size of the introns by restriction endonuclease digestion.

E. Expression of eps15 Gene

Following isolation and characterization of the eps15 gene, it is routine to express that gene in a recombinant organism to obtain significant amounts of eps15. One example of a suitable expression vector and host is set forth in Example 4. Alternatively, the DNA encoding eps15 can be inserted into other conventional host organisms and expressed. The organism can be a bacterium, yeast, cell line, or multicellular plant or animal. The literature is replete with examples of suitable host organisms and expression techniques. For example, naked polynucleotide (DNA or mRNA) can be injected directly into muscle tissue of mammals, wherein it is expressed. This methodology can be used to deliver the polynucleotide and, therefore, the resulting polypeptide translation product to the animal, or to generate an immune response against a foreign polypeptide (Wolff et al., *Science* 247:1465 (1990); Felgner et al., *Nature* 349:351 (1991)). Alternatively, the coding sequence, together with appropriate regulatory regions (i.e., a construct), can be inserted into a vector, which is then transfected into a cell. The cell (which may or may not be part of a larger organism) then expresses the polypeptide.

F. Invivo Transcription of eps15

In order to assess the expression of mRNA encoded by the murine eps15 gene, we performed Northern blot analysis of poly(A)+ RNA extracted from NIH-3T3 cells using the pl 15 insert as a probe. Two major bands of −3.3 and −6.0 kb were detected. The size of the smaller band was in agreement with that of the eps15 cDNA clone. The nature of the 6.0 kb band was not resolved. It is unlikely that the band represents a related species since hybridization was performed under high stringency conditions. Thus, it most likely represents a partially processed precursor or an alternatively spliced form of the transcript.

G. Assays for Detecting eps15

Antibodies generated against the eps15 polypeptide can be obtained by direct injection of the naked polynucleotide into an animal (Wolff et al., *Science* 247:1465 (1990)) or by administering the polypeptide to an animal, as explained in Example 4. The antibody so obtained will then bind the polypeptide itself. In this manner, even a sequence encoding only a fragment of eps15 can be used to generate antibodies binding the entire native polypeptide.

Antibodies generated in accordance with Example 4 can be used in standard immunoassay formats to detect the presence and/or amount of eps15 in a sample. Such assays can comprise competitive or noncompetitive assays. Radioimmunoassays, ELISAS, Western Blot assays, immunohistochemical assays, immunochromatographic assays, and other conventional assays are expressly contemplated. Furthermore, polyclonal antibodies against human or other eps15 can be readily generated using the techniques of Example 4, and monoclonal antibodies to any form of eps15 can be generated using well-known methods. All of these antibodies can be used in assays of the present invention. The assays and the antibodies discussed herein form an embodiment of this invention.

H. Detection of TKR Kinase Activity

In many instances, it is important to know the TKR tyrosine kinase activity of a sample. The present invention provides a ready method by which such activity can be determined. As discussed in more detail infra, eps15 is tyrosine phosphorylated by the EGFR as well as by other tyrosine kinase receptors. This ability of TKRs to phosphorylate eps15 is exploited to measure the presence of TKRs in a sample.

Briefly, one method for such measurement is to contact a sample with eps15, add radiolabeled γ-ATP to the sample and then measure the extent to which the radiolabel is incorporated into the eps15. Anti-eps15 antibodies may be used in the final step of the assay to capture eps15 for measurement of phosphbrylation. Such assays are disclosed in more detail in Examples 9 and 10.

I. Differential Phosphorylation of eps15 by the EGFR and erbB-2 Kinase

As discussed in more detail herein, eps15 is tyrosine phosphorylated by the EGFR kinase and much less efficiently by the highly related $gp185^{erbB-2}$ kinase, an unexpected finding in light of the high degree of homology between these two kinases.

The availability of anti-eps15 antibodies permitted testing of the specificity of eps15 phosphorylation by the EGFR and erbB-2 kinases. Tyrosine phosphorylation of the major species of the eps15 gene product, $p142^{eps15}$, was, measured. Two mass populations of NIH-3T3 cells transfected either with EGFR or with the EGFR/erbB-2 chimera containing the extracellular domain of EGFR and the intracellular domain of erbB-2 were utilized (Fazioli et al., *Mol. Cell. Biol.* 11:2040–2048 (1991); Lee et al., *EMBO J.* 8:167–173 (1989); Lehvaslaiho et al., *EMBO J.* 8:159–166 (1989); Lonardo et al., *New Biol.* 2:992–1003 (1990)). The NIH-EGFR and NIHEGFR/erbB-2 lines expressed comparable number of receptors and exhibited similar affinity for EGF binding, thus allowing rigorous quantitative analysis of the in vitro phosphorylation events triggered by EGF stimulation.

EGF treatment of NIH-EGFR/erbB-2 cells resulted in little if any tyrosine phosphorylation of $p142^{eps15}$, although it induced readily detectable autophosphorylation of the chimeric receptor and phosphorylation of a number of other intracellular proteins. Conversely, EGF stimulation of NIHEGFR promptly triggered $p142^{eps}15$ tyrosine phosphorylation. The differential response of NIH-EGFR and NIH-EGFR/erbB-2 could not be ascribed to intrinsic differences in the two cell lines, since PDGF stimulation was able to elicit $p142^{eps15}$ phosphorylation in both of them. It was concluded, therefore, that the erbB-2 kinase is much less efficient than the EGFR at stimulating tyrosine phosphorylation of $p142^{eps15}$.

A panel of chimeric-molecules constructed from regions of the EGFR and erbB-2 kinase was employed to map the portion(s) of these receptors responsible for the differential tyrosine phosphorylation of eps15 by EGFR and erbB-2. The chimerae were engineered by substituting domains of $gp185^{erbB-2}$ for the corresponding regions of the EGFR and have been previously described and characterized (Di Fiore et al., *Cell* 51:1063–1070 (1987); Di Fiore et al., *Mol. Cell. Biol.* 10:2749–2756 (1990); Di Fiore et al., *Science* 248:7983 (1990); Segatto et al., *Mol. Cell. Biol.* 11:3191–3202 (1991)). An EGFR/erbB-$2^{COOH}$ chimera, in which the carboxyl terminal (COOH) domain of $gp185^{erbB-2}$ was substituted for the COOH domain of EGFR, was able to phosphorylate eps15 comparably to the wild type EGFR. Conversely, the substitution of the tyrosine kinase (TK) region of $gp185^{erbB-2}$ into EGFR (EGFR/erbB-$2^{TK}$) yielded a molecule which was severely impaired in its ability to phosphorylate eps15. Further mapping showed that the substitution of the first ⁻150 amino acid of $gp185^{erbB-2}$ for the analogous region of EGFR (juxtamembrane or TK-1 domain) was alone sufficient to decrease the ability of the chimeric EGFR/erbB-$2^{TK1}$ receptor to phosphorylate eps15.

These differences were not due to different levels of expression of the chimeric molecules and wild type EGFR in NIH-3T3 transfectants, as shown by $^{125}$I-EGF binding experiments, nor to differences in the levels of eps15 expressed in the various transfectants. In addition, it has previously been shown that all of the employed chimerae possess in vivo tyrosine kinase activity as demonstrated by efficient autophosphorylation and competence at phosphorylating intracellular substrates, including PLC-γ (Fazioli et al., *Mol. Cell. Biol.* 11:2040–2048 (1991); Segatto et al., *Mol. Cell. Biol.* 11:3191–3202 (1991); Di Fiore et al., *Mol. Cell. Biol.* 10:2749–2756 (1990)), and ability to deliver sizable mitogenic signals in NIH-3T3 cells (Di Fiore et al., *Mol. Cell. Biol.* 10:2749–2756 (1990); Segatto et al., *Mol. Cell. Biol.* 11:3191–3202 (1991); Fazioli et al., *Mol. Cell. Biol.* 11:2040–2048 (1991); Di Fiore et al., *Science* 248:79–83 (1990)). It was concluded, therefore, that the juxtamembrane (or TK-1) region of the EGFR contains the determinants responsible for efficient phosphorylation of eps15.

The mechanisms by which the EGFR phosphorylates the eps15 gene product remain to be established. In repeated experiments, co-immunoprecipitation of these two proteins was not detected. This indicates either phosphorylation by a second kinase, activated by the EGFR, or disruption of the EGFR/eps15 complex even under the mild lysis conditions employed in the co-immunoprecipitation experiments. It is widely accepted now that detergent-resistant interactions between TKRs and some of their substrates are made possible by binding of specialized regions of substrate molecules, known as SH2 domains, to phosphotyrosine motifs present in TKRs (Koch et al., *Science* 252:668–674 (1991)). To this regard, it is noted that the eps15 cDNA describes the synthesis of a protein lacking SH2 domains. The SH2/pTyr interactions, however, may not be the sole ones responsible for receptor/substrate interactions, and others, possibly of a weaker type, might exist. There is now evidence that purified EGFR can directly phosphorylate bacterially expressed $p142^{eps\ 15}$ in invitro assays (W. Wong and P. P. Di Fiore, unpublished observations).

J. Detection of Altered Mitogenic Signal Transduction

The eps15 of the present invention is also valuable in detection of altered mitogenic signal transduction. Such altered signal transduction can be ascertained by measurement of eps15 levels in vivo or in vitro using the immunoassays discussed above. Alternatively, altered forms of eps15 can be detected by using at least a portion of the DNA encoding eps15 as a probe to isolate the DNA encoding a possibly altered form of eps15. Techniques of the type disclosed in Examples 2 and 3, or other conventional techniques, can then be used to sequence the isolated DNA. By comparing this sequence to the known sequence, alterations can be detected.

If an altered eps15 sequence or abnormal levels of eps15 are detected in malignant tissue, antisense therapy can be utilized in accordance with Example 11 to halt translation of the protein, or triple helix therapy in accordance with Example 12 to shut-off RNA transcription, and, thus, in both cases, to interfere with mitogenesis.

K. Increasing the Mitogenic Response of Cells

We have also discovered that the mitogenic response of cells to mitogenic factors can be enhanced by delivering eps15 to the cell in amounts greater than the natural amounts. The optimum dosage for any particular cell type can be empirically determined in a relatively straightforward manner. It is apparent that an increased dosage will have a mitogenesis-enhancing effect as demonstrated by the observation that overexpression of eps15 is sufficient to transform NIH-3T3 cells.

Particular aspects of the invention may be more readily understood by reference to the following examples, which are intended to exemplify the invention, without limiting its scope to the particular exemplified embodiments.

EXAMPLE 1

Generation of Polyclonal Antibody Against EGFR Substrates

Immunoaffinity chromatography techniques were used to isolate proteins which were tyrosine phosphorylated by EGFR, as described by Fazioli et al., *J. Biol. Chem.* 267:5155–5161 (1992). Briefly, genetically engineered NIH-3T3 cells which overexpress EGFR (NIH-EGFR) (Fazioli et al., *Mol. Cell Biol.* 11:2040–2048 (1991)) were maintained in DMEM (Gibco, Gaithersburg, Md.) supplemented with 10% calf serum (Gibco, supra). Subconfluent cell monolayers were treated with EGF (Upstate Biotechnology, Inc. (UBI), Lake Placid, N.Y.), and lysed. EGFR was removed from the lysate using an anti-EGFR column prepared by linking anti-EGFR monoclonal antibody (Ab1, Oncogene Science, Uniondale, N.Y.) to agarose beads. The lysate was then contacted with an anti-phosphotyrosine (anti-pTyr, Oncogene Science, supra) column; the column was washed; and the bound protein was then eluted. Fractions were collected and were used to immunize two New Zealand white rabbits, yielding two polyclonal immune sera, designated 450 and 451.

EXAMPLE 2

Identification of eps15 CDNA Clone

A pool of sera 450 and 451 from Example 1 was used to screen a commercial (Clontech, Palo Alto, Calif.) λgt11 library from NIH-3T3 cells. Recombinant plaques ($10^6$) were initially screened with a 1:200 dilution of each antibody in TTBS (0.05% Tween 20 mM Tris-HCl [pH 7.5] 150 mM NaCl) containing 1% BSA. Detection was carried out with a goat anti-rabbit Ab conjugated to alkaline phosphatase by utilizing a commercial kit (Picoblue, Stratagene, La Jolla, Calif.) according to the manufacturer's specification. Analysis yielded several positive plaques; one of these clones (pl 15) contained an insert of ~1.8 kbp which was completely sequenced and had no correspondence to sequences present in the Genbank or EMBL data banks. The pl 15 insert was subcloned in the Eco RI site of pBluescript® (Stratagene, supra).

The sequence of pl 15 predicted an ORF which started in the expected frame with the β-galactosidase portion of λgt11 but contained neither an initiation nor a stop codon. It was concluded that pl 15 represented a partial cDNA encoding a novel protein, now designated eps15 (for EGFR pathway substrate #15).

EXAMPLE 3

Isolation and sequencing of eps15 CDNA

Full length CDNA for eps15 (pCEV-eps15) was obtained by screening a mouse keratinocyte CDNA library (Miki et al., *Science* 251:72–75 (1991)) using the pl 15 insert from Example 2 as a probe according to standard procedures (Sambrook et al., *Molecular Biology: A Laboratory Manual* (Cold Spring Harbor Laboratory Press 1989). DNA sequencing was performed by the dideoxy-termination method on both strands of the cDNA, using a commercial kit (SEQUENASE®, United States Biochemical, Cleveland, Ohio). The resulting DNA sequence is identified as SEQ ID NO:3. The 3033 bp sequence was found to contain a stop codon at position 2802–2804 followed by a 3' untranslated sequence containing a putative polyadenylation site (AATTAAA) starting at position 3014. The first in-frame ATG (position 111–113) conformed to Kozak's rules for translational initiation (Kozak M., *J. Cell Biol.* 108:229–241 (1989)) and was preceded by 110 bp of 5' untranslated sequence.

EXAMPLE 4

Preparation of Anti-eps15 Antibody and Expression of eps15 Gene Product

Polyclonal antibodies specific for the eps15 gene product were generated against a recombinant trpE fusion protein. To this end the open reading frame (ORF) of pl 15, positioned between two Eco RI sites, was cloned in frame in the Eco RI site of the pATH 11 bacterial expression vector. The recombinant fusion protein was expressed by induction with indoleacrylic acid (Koerner et al., *Methods Enzymol.* 194:477–490 (1991)), gel purified and used to immunize New Zealand rabbits. A commercially available antiphosphotyrosine (anti-pTyr) monoclonal antibody (Upstate Biotechnology, Lake Placid, N.Y.) was also used. Specificity of detection for anti-pTyr was controlled as described previously (Fazioli et al., *J. Biol. Chem.* 267:5155–5161 (1992); Fazioli et al., *Mol. Cell Biol.* 11:2040–2048 (1991), which are both incorporated by this reference).

The anti-eps15 serum specifically recognized a major species of Mr 142 kDa ($p142^{eps15}$) and a minor component of 155 kDa ($p155^{eps15}$) in NIH-EGFR cells. A second doublet of much lower intensity, migrating as 119–122 kDa, was also specifically recognized by the anti-eps15 serum. The size of the major eps15 band (142 kDa) was significantly larger than that of the deduced protein (approximately 98 kDa). This difference is not due to N-linked glycosylation, since no differences in the electrophoretic mobility of eps15 were detectable after tunycamicin treatment. In addition, in vivo transcription and translation of the pCEV-eps15 cDNA yielded a protein comigrating with authentic $p142^{eps15}$. Therefore, the discrepancy between the actual and deduced size of eps15 should be ascribed to either abnormalities in its gel migration, or to post-translational modification still occurring in a reticulocytes lysate. Analysis of sequential immunoprecipitation and immunoblotting with anti-pTyr and anti-eps15 antibodies of lysates prepared from NIH-EGFR cells, before and after in vitro EGF treatment, indicated that both $p142^{eps15}$ and $p155^{eps15}$ were phosphorylated in vitro on tyrosine following EGFR activation.

Anti-pTyr recovery of the eps15 product might be due to direct recognition of phosphotyrosil residues or to association with other pTyr-containing proteins. To distinguish between these possibilities immunoprecipitation experiments with anti-eps15 were performed, followed by immunoblot with anti-pTyr. It was found that $p142^{eps15}$ was readily detectable under these conditions in cell lysates obtained from NIH-EGFR cells triggered with EGF; $p142^{eps15}$ was not detectable in cell lysates from untreated cells. Under these same conditions, it was not easy to detect p155$^{eps15}$ in EGF-treated NIH-EGFR cells due to the presence of a superimposed background band in experiments on cell lysates from untreated cells. Nevertheless, these results established that eps15 is tyrosine phosphorylated following EGFR activation.

EXAMPLE 5

Derivation of Partial Human eps15 Sequence

The partial human eps15 sequence was obtained by the polymerase chain reaction (PCR) method using two oligonucleotides from the mouse eps15 cDNA sequence as primers to amplify the human cDNA fragment from a human cDNA library. The library used was from A101D cells (human melanoma cells, Giard et al., *J. Nat'l Cancer Institute* 51:1417–1423 (1973)), although other readily-available libraries could be used. The library was prepared using the method of Miki et al., *Science* 251:72–75 (1991). The two oligonucleotide PCR primers were:
1) 5' CGAGCTCGAGGTGCATCCAGCAACAGCAGTA
2) 5' CGATATCGATTTGCTTGGGTCAGCCTCTTTA
and included sequences corresponding to positions 2137–2157 and 2618–2638 of the mouse eps15 cDNA sequence (SEQ ID NO:3), respectively. A typical PCR contained 100 ng of cDNA library DNA, 5 units of Taq DNA polymerase (Boehringer Mannheim, Indianapolis, Ind.), 1 $\mu$M of each oligonucleotide primer, 200 $\mu$M dNTPs, 10 mM Tris-HCl (pH 8.3), 1.5 mM MgCl$_2$, 50 mM KCl, 0.1 mg/ml gelatin. Reactions were carried out for 35 cycles of 1.5 min at 94° C., 5 min at 50° C., and 2 min at 72° C. Reactions were then terminated with an additional 10 min at 72° C. The PCR products were purified by chroma spin+TE-400 column (Clontech, Palo Alto, Calif.), subcloned into pBluescript® II KS vector (Stratagene, La Jolla, Calif.), and sequenced by the dideoxy-termination methods on both strands using the SEQUENASE® DNA sequencing kit (USB, Cleveland, Ohio).

EXAMPLE 6

Identification of Human eps15 CDNA clone

A PCR-amplified fragment of 519 bp, acquired in accordance with Example 5, was used to screen a human cDNA library from M426 cells, although other readily available libraries could be used. Several clones were isolated and the longest cDNA (SEQ ID NO:1) was DNA- sequenced by the dideoxy-termination method, as explained in Example 3. The human eps15 clone obtained was 4165 nucleotides long and possessed an ATG at positions 21–23 which conformed to Kozak's rules for translation initiation (Kozak et al., *J. Cell. Biol.* 108:229–241 (1989)). The clone displayed a stop codon at position 2709–2711. It was not determined whether this was a full length clone, but it encompassed the entire open reading frame of eps15, as established by comparison to the mouse CDNA.

EXAMPLE 7

Isolation of eps15 sequences from other Organisms

Two potentially complementary strategies are used to isolate and clone the eps15 gene in other species. The first strategy is essentially the same as the one used to obtain the human eps15 sequence. Briefly, two oligonucleotides from the mouse or the human eps15 sequence can be used to PCR amplify fragments of eps15 CDNA from other species. The oligonucleotides can be designed from regions of high nucleotide identity between the human and mouse sequence, in a way to increase the probability of obtaining an efficient matching of the primers with the eps15 sequences of other species. Alternatively, degenerate PCR primers can be used to amplify sequences similar to the mouse or human gene. The template for the PCR reaction can be a CDNA library from cells of another species or a CDNA obtained by reverse transcriptase (in the so called reverse transcriptase/PCR method) directly from the mRNA of another species. A second approach relies on classical low stringency hybridization of nucleic acids. In this case a probe representing the eps15 CDNA from human or mouse is hybridized, under relaxed conditions of stringency, against libraries (cDNA or genomic) prepared from cells of other species. Relaxed stringency is obtained by modifying the temperature and the ionic strength of the hybridization buffer by well known methods, in a manner designed to allow stable formation of hybrids which are not 100% matching (as expected in interspecies hybridization). The positives are then analyzed as described above (see Example 6). A complete review on low stringency hybridization is to be found in Kraus et al., *Methods in Enzymology* 200:546–556 (1991).

According to Kraus, standard high-stringency hybridization is conducted in 5×SSC (1×SSC=0.15 M NaCl, 0.015 M sodium citrate, pH 7) and 50% formamide at 42°, which establishes conditions 20°–25° below the T$_m$ (melting point) of a completely matched DNA hybrid For hybridization the membrane is place in a sealing bag, wetted in two-thirds of the final volume (0.075 ml/cm$_2$ filter area), and probe is added in the remaining third of hybridization solution. The bag is sealed and after thorough mixing of the solutions placed between two glass plates in a 42° water bath for 8–16 hr.

Hybridization solution (1×): 5×SSC, 1-% (w/v) dextran sulfate, 2.5×Denhardt's solution, 10 mM Tris pH 7.4, 50 $\mu$g/ml sheared and boiled salmon sperm DNA, 50% (v/v) formamide, 2–5×10$^6$ cpm/ml at a DNA concentration of <5 ng/ml.

Hybridization buffer containing SSC, dextran sulfate, Denhardt's, and Tris is prepared as 2×stock solution by dissolving dextran sulfate powder in SSC while stirring prior to adding the other components. Nonradioactive and radioactive hybridization solutions are prepared by adding salmon sperm DNA to the formamide, and purified probe is added to the latter solution. Both are then incubated 5 min at 50°, thoroughly mixed, and hybridization buffer is added to 1×final concentration. This step will ensure sufficient denaturation of both carrier and labeled probe DNA. For reduced stringency hybridization, the volume is adjusted with water following denaturation in formamide. High specific activity probes of >10$^8$ cpm/$\mu$g DNA can be routinely obtained with commercially available nick translation (i.e., Amersham, Arlington Heights, Ill.) or random primer kits. Under these conditions "prehyridization" of the filter is not required, as long as the filter is prewefted in nonradioactive hybridization solution prior to adding the probe.

After hybridization, filters are washed three times for 5 min each in 2×SSC, 0.01% SDS at room temperature. Two high-stringency washes of 20 min each are then conducted at 50° in 0.1×SSC/0.1%SDS and 0.1×SSC, respectively.

Thus, to determine experimentally the optimal stringency for cross-hybridization of a novel related tyrosine kinase gene, it proves useful to subject replica nitrocellulose filters containing genomic DNA to hybridization under stringencies incrementally decreased by 7°. Discrete intermediate levels of reduced stringency (Table I) may be useful in some cases. Since stringency is presumed to affect predominantly the formation of hybrids during hybridization and the stability of hybrids during washing, both hybridization and washing are conducted under equally reduced stringencies. Experimentally these are controlled by the formamide concentration during hybridization and salt concentration during washing, respectively, with otherwise identical conditions (Table I).

It is helpful to relate stringency in temperature degrees (°C.) assuming that decrease of formamide concentration by 1% increases the $T_m$ of the hybrid by 0.7° and a logfold increase in ionic strength raises the stability of a hybrid by 18.5°. Thus, considering incubation temperature ($T_i$), formamide concentration (FA), and ionic strength ($\mu$), experimental stringency conditions relative to high-stringency hybridization can be approximated as $$T_s = T_i + 0.7(\%FA) - 18.5 \log (\mu/\mu_0)$$

where $T_s$ is the stringency expressed as temperature degrees, $T_i$, the incubation temperature, and $\mu$ the ionic strength, while $\mu_0$ represents the ionic strength during hybridization conditions equalling 1 M Na$^+$ (5xSSC). At these high salt concentrations the hybrid stability is maximal and relatively unaffected by variations of ionic strength (log 1=0). Under high-stringency conditions the estimated $T_s$ of the hybridization ($T_s = 42° + 0.7° \times 50 - 18.5 \times \log 1$) is 77° and the $T_s$ during washing ($T_s = 50° + 0.7° \times 0 - 18.5° \times \log 0.02$) is 81°. Reducing the formamide concentration by 10% results in an estimated stringency of $T_s = 70°$, yielding a stringency reducing of $\Delta T_s = -7°$ in the hybridization. Equivalent reduction of the washing stringency requires an increase of the salt concentration to 0.25xSSC (0.05 M Na$^+$) Table I lists experimental conditions with the respective estimated reduction in stringency achieved simultaneously during hybridization and washing. Since the rate of filter hybridization is not affected by formamide concentrations in the range from 50 to 30% and only slightly reduced at 20% formamide, hybrid formation at different stringencies mainly depends on the degree of mismatches between probe and template DNA, eliminating hybridization kinetics as a major variable. Under these experimental conditions, we observed comparable signal/noise ratios at both high and reduced stringency

TABLE I

| Stringency Reduction[a] | | |
|---|---|---|
| Stringency reduction ($\Delta T_s$)(°C.) | Hybridization (42°/5xSSC) | Washing (50°) |
| 0 | 50% FA | 0.1xSSC->0.02 M Na$^+$ |
| -3.5 | 45% FA | 0.15xSSC->0.03 M Na$^+$ |
| -7 | 40% FA | 0.25xSSC->0.04 M Na$^+$ |
| -10.5 | 35% FA | 0.4xSSC->0.08 M Na$^+$ |
| -14 | 30% FA | 0.6xSSC->0.12 M Na$^+$ |
| -17.5 | 25% FA | 1xSSC->0.2 M Na$^+$ |
| -21 | 20% FA | 1.5xSSC->0.3 M Na$^+$ |

[a]$\Delta T_s$ indicates reduction of stringency relative to high-stringency conditions (bold type). FA, Formamide; 1xSSC = 0.15 M NaCl, 0.015 M sodium citrate, pH7. For each stringency, hybridization is conducted at 42° in 5xSSC, while washing occurs at 50°.

EXAMPLE 8

Quantitative Immunoassay for eps15

It is often desirable to determine the quantity of eps15 in a sample. This can be particularly useful in clinical research, as well as in detecting abnormalities in mitogenic signal transduction in malignant tissue. Additionally, in many human tumors, tumor markers are released in the blood stream at levels which correlate with the size of the tumor and its clinical stage. Determining the levels of markers (such as eps15) in biological fluids can be advantageous in aiding the diagnostic procedures and in monitoring the effectiveness of therapy.

In one exemplary technique, anti-eps15 antibody from Example 4 is immobilized to an agarose column, as explained in Example 1. Sample is then directed through the column where eps15 in the sample is bound by the immobilized antibody. Next, a known quantity of radiolabeled anti-eps15 antibody is directed through the column. The quantity of labeled antibody which is not retained on the column is measured, and bears a relationship to the quantity of eps15 in the sample.

Another exemplary technique is liquid phase radioimmunoassay. First, a standard measurement is made by challenging a known amount of purified eps15, radiolabeled in a conventional manner, against a known amount of anti-eps15 antibody. The resulting immunocomplex is recovered by centrifugation, and the radioactivity of the centrifugate is determined. This value is used as a standard against which later measurements are compared.

Next, a sample, containing an unknown amount of eps15, is challenged against the same known amount (used in making the standard measurement) of anti-eps15 antibody. Then, the same amount of labeled eps15 used in making the standard measurement is added to the reaction mixture, followed by centrifugation and measurement of radioactivity as explained above. The decrease in the immunoprecipitated radioactivity (in comparison to the standard) is proportional to the amount of eps15 in the sample.

Of course, in addition to the foregoing exemplary methods, any of the well known conventional immunoassay methods may similarly be used.

EXAMPLE 9

Assay for Phosphorylation of eps15 by TKRs

A biological sample is assayed for TKR tyrosine kinase activity by combining the sample with known quantities of eps15 and $^{32}$P-labeled $\gamma$-ATP. The sample is then contacted with anti-eps15 from Example 4 immobilized on a column; the column is washed; and the bound eps15 is eluted with 0.1M glycine, pH 2.5. The eluant is then subjected to fractionation to separate the resulting radiolabeled eps15 from the free radioactivity in the sample using any conventional technique, such as precipitation in 5–10% trichloroacetic acid. Following fractionation, the amount of radioactivity incorporated into the eps15 is counted to measure TKR tyrosine kinase activity of the sample.

EXAMPLE 10

Alternative Assay for TKR Tyrosine Kinase Activity 100 ng of eps15 is added to 1 ml buffered cell lysate suspected of having TKR tyrosine kinase activity, together with 30 $\mu$C $^{32}$P-$\gamma$ATP. Following incubation, the mixture is heated to 100° C. in a solution containing sodium lauryl sulfate (SDS) and $\beta$-mercaptoethanol. Aliquots are electrophoresed on 10–15% gradient SDS polyacrylamide gels and exposed to X-Omat X-ray film to identify radioactive eps15. Cell lysate from eps15-transfected cells incubated in the

17 presence of radiolabeled amino acids is used to confirm the location on the gel of the phosphorylated eps15.

EXAMPLE 11

Preparation and Use of Antisense oligonucleotides

Antisense RNA molecules are known to be useful for regulating translation within the cell. Antisense RNA molecules can be produced from the sequences of the present invention. These antisense molecules can be used as therapeutic agents to regulate gene expression.

The antisense molecules are obtained from a nucleotide sequence by reversing the orientation of the coding region with regard to the promoter. Thus, the antisense RNA is complementary to the corresponding mRNA. For a review of antisense design see Green et al., *Ann. Rev Biochem.* 55:569–597 (1986), which is hereby incorporated by reference. The antisense sequences can contain modified sugar phosphate backbones to increase stability and make them less sensitive to RNase activity. Examples of the modifications are described by Rossi et al., *Pharmocol. Ther.* 50:245–254, (1991).

Antisense molecules are introduced into cells that express the eps15 gene. In a preferred application of this invention, the effectiveness of antisense inhibition on translation can be monitored using techniques that include, but are not limited to, antibody-mediated tests such as RIAs and ELISA, functional assays, or radiolabeling. The antisense molecule is introduced into the cells by diffusion or by transfection procedures known in the art. The molecules are introduced onto cell samples at a number of different concentrations, preferably between $1 \times 10^{-7}$ M $1 \times 10^{-4}$ M. Once the minimum concentration that can adequately control translation is identified, the optimized dose is translated into a dosage suitable for use in vivo. For example, an inhibiting concentration in culture of $1 \times 10^{-7}$ M translates into a dose of approximately 0.6 mg/kg bodyweight. Levels of oligonucleotide approaching 100 mg/kg bodyweight or higher may be possible after testing the toxicity of the oligonucleotide in laboratory animals.

The antisense molecule can be introduced into the body as a bare or naked oligonucleotide, oligonucleotide encapsulated in lipid, oligonucleotide sequence encapsidated by viral protein, or as oligonucleotide contained in an expression vector. The antisense oligonucleotide is preferably introduced into the vertebrate by injection. Alternatively, cells from the vertebrate are removed, treated with the antisense oligonucleotide, and reintroduced into the vertebrate. It is further contemplated that the antisense oligonucleotide sequence is incorporated into a ribozyme sequence to enable the antisense to bind and cleave its target. For technical applications of ribozyme and antisense oligonucleotides, see Rossi et al., supra.

EXAMPLE 12

Preparation and Use of Triple Helix Probes

Triple helix oligonucleotides are used to inhibit transcription from a genome. They are particularly useful for studying alterations in cell activity as it is associated with a particular gene. The eps15 sequence or, more preferably, a portion thereof, can be used to inhibit gene expression in individuals suffering from disorders associated with the eps15 gene similarly, a portion of the eps15 gene sequence, or the entirety thereof, can be used to study the effect of inhibiting transcription of the gene within a cell. Traditionally, homopurine sequences were considered the most useful. However, homopyrimidine sequences can also inhibit gene expression. Thus, both types of sequences corresponding to the eps15 gene are contemplated within the scope of this invention. Homopyrimidine oligonucleotides bind to the major groove at homopurine:homopyrimidine sequences. As an example, 10-mer to 20-mer homopyrimidine sequences from the eps15 gene can be used to inhibit expression from homopurine sequences. Moreover the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al., *Science* 245:967–971 (1989), which is hereby incorporated by this reference.

The oligonucleotides may be prepared on an oligonucleotide synthesizer or they may be purchased commercially from a company specializing in custom oligonucleotide synthesis. The sequences are introduced into cells in culture using techniques known in the art that include but are not limited to calcium phosphate precipitation, DEAE-Dextran, electroporation, liposome-mediated transfection or native uptake. Treated cells are monitored for altered cell function. Alternatively, cells from the organism are extracted, treated with the triple helix oligonucleotide, and reimplanted into the organism.

While particular embodiments of the invention have been described in detail, it will be apparent to those skilled in the art that these embodiments are exemplary rather than limiting, and the true scope of the invention is that defined within the attached claims.

What is claimed is:

1. A purified antibody that specifically binds to the amino acid residues of human eps15, said human eps15 having the amino acid sequence of SEQ ID NO:2.

2. A purified antibody that specifically binds to the amino acid residues of murine eps15, said murine eps15 having the amino acid sequence of SEQ ID NO:4.

3. A purified antibody that specifically binds to the amino acid residues of eps15, said eps15 having an amino acid sequence encoded by DNA that hybridizes under low stringency hybridization conditions to the protein-encoding domain of SEQ ID NO:1 or SEQ ID NO:3, and said eps15 serving as a substrate for tyrosine phosphorylation following Epidermal Growth Factor Receptor (EGFR) activation, wherein said low stringency hybridization conditions are conducted by controlling the formamide concentration during hybridization and salt concentration during washing according to Table I.

4. The antibody according to claim 1, 2, or 3, wherein said antibody is monoclonal.

5. The antibody according to claim 1, 2, or 3, purified to a concentration of at least 0.01% by weight.

6. The antibody according to claim 1, 2, or 3, purified to a concentration of at least 0.1% by weight.

7. The antibody according to claim 1, 2, or 3, purified to a concentration of at least 0.5% by weight.

8. The antibody according to claim 1, 2, or 3, purified to a concentration of at least 1% by weight.

9. The antibody according to claim 1, 2, or 3, purified to a concentration of at least 5% by weight.

10. The antibody according to claim 1, 2, or 3, purified to a concentration of at least 10% by weight.

11. The antibody according to claim 1, 2, or 3, purified to a concentration of at least 20% by weight.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4165 base pairs
        ( B ) TYPE: nucleic acid
        ( C ) STRANDEDNESS: double
        ( D ) TOPOLOGY: linear (ii) MOLECULE TYPE: cDNA (iii) HYPOTHETICAL: NO (iv) ANTI-SENSE: NO (ix) FEATURE:
  (A) NAME/KEY: CDS
  (B) LOCATION: 21..2709

(xi) SEQUENCE DESCRIPTION: SEQ ID NO:1:

```
AACCGCATGA TGGAAACACC ATG GCT GCG GCG GCC CAG CTC TCT CTG ACA          50
                      Met Ala Ala Ala Ala Gln Leu Ser Leu Thr
                       1                  5                 10

CAG TTA TCA AGT GGG AAT CCT GTA TAT GAA AAA TAC TAT AGA CAG GTT        98
Gln Leu Ser Ser Gly Asn Pro Val Tyr Glu Lys Tyr Tyr Arg Gln Val
                 15                  20                  25

GAT ACA GGC AAT ACT GGA AGG GTG TTG GCT TCT GAT GCT GCT GCT TTC       146
Asp Thr Gly Asn Thr Gly Arg Val Leu Ala Ser Asp Ala Ala Ala Phe
             30                  35                  40

CTG AAA AAA TCA GGG CTT CCA GAC TTG ATA CTT GGA AAG ATT TGG GAT       194
Leu Lys Lys Ser Gly Leu Pro Asp Leu Ile Leu Gly Lys Ile Trp Asp
         45                  50                  55

TTA GCC GAC ACA GAT GGC AAA GGT ATC CTG AAC AAA CAA GAA TTC TTT       242
Leu Ala Asp Thr Asp Gly Lys Gly Ile Leu Asn Lys Gln Glu Phe Phe
     60                  65                  70

GTT GCT TTG CGT CTT GTG GCA TGT GCC CAG AAT GGA TTG GAA GTT TCA       290
Val Ala Leu Arg Leu Val Ala Cys Ala Gln Asn Gly Leu Glu Val Ser
 75                  80                  85                  90

CTA AGT AGT TTG AAC CTG GCT GTT CCT CCA CCA AGA TTT CAT GAT ACC       338
Leu Ser Ser Leu Asn Leu Ala Val Pro Pro Pro Arg Phe His Asp Thr
                 95                 100                 105

AGT AGT CCT TTG CTA ATC AGT GGA ACC TCT GCA GCT GAG CTC CCA TGG       386
Ser Ser Pro Leu Leu Ile Ser Gly Thr Ser Ala Ala Glu Leu Pro Trp
             110                 115                 120

GCT GTA AAA CCT GAA GAT AAG GCC AAA TAT GAT GCA ATA TTT GAT AGT       434
Ala Val Lys Pro Glu Asp Lys Ala Lys Tyr Asp Ala Ile Phe Asp Ser
         125                 130                 135

TTA AGC CCA GTG AAT GGA TTT CTG TCT GGT GAT AAA GTG AAA CCA GTG       482
Leu Ser Pro Val Asn Gly Phe Leu Ser Gly Asp Lys Val Lys Pro Val
     140                 145                 150

TTG CTC AAC TCT AAG TTA CCT GTG GAT ATC CTT GGA AGA GTT TGG GAG       530
Leu Leu Asn Ser Lys Leu Pro Val Asp Ile Leu Gly Arg Val Trp Glu
155                 160                 165                 170

TTG AGT GAT ATT GAC CAT GAT GGA ATG CTT GAC AGA GAT GAG TTT GCA       578
Leu Ser Asp Ile Asp His Asp Gly Met Leu Asp Arg Asp Glu Phe Ala
                 175                 180                 185

GTT GCC ATG TTT TTG GTA TAC TGT GCA CTG GAG AAA GAA CCT GTG CCA       626
Val Ala Met Phe Leu Val Tyr Cys Ala Leu Glu Lys Glu Pro Val Pro
             190                 195                 200

ATG TCC TTG CCT CCA GCC TTG GTG CCA CCA TCT AAG AGA AAA ACG TGG       674
Met Ser Leu Pro Pro Ala Leu Val Pro Pro Ser Lys Arg Lys Thr Trp
         205                 210                 215

GTT GTA TCC CCT GCA GAA AAA GCT AAA TAT GAT GAA ATC TTC CTG AAA       722
Val Val Ser Pro Ala Glu Lys Ala Lys Tyr Asp Glu Ile Phe Leu Lys
     220                 225                 230

ACT GAT AAA GAT ATG GAC GGA TTT GTG TCT GGA TTG GAG GTC CGT GAA       770
Thr Asp Lys Asp Met Asp Gly Phe Val Ser Gly Leu Glu Val Arg Glu
235                 240                 245                 250

ATA TTC TTG AAA ACA GGT TTA CCT TCT ACC TTA CTA GCC CAT ATA TGG       818
Ile Phe Leu Lys Thr Gly Leu Pro Ser Thr Leu Leu Ala His Ile Trp
                 255                 260                 265
```

| | | | | | | | | | | | | | | | | |
|---|---|---|---|---|---|---|---|---|---|---|---|---|---|---|---|---|
| TCA | TTA | TGC | GAC | ACA | AAG | GAC | TGT | GGG | AAG | CTT | TCA | AAG | GAT | CAG | TTT | 866 |
| Ser | Leu | Cys | Asp 270 | Thr | Lys | Asp | Cys 275 | Gly | Lys | Leu | Ser | Lys 280 | Asp | Gln | Phe | |
| GCC | TTG | GCT | TTT | CAC | TTA | ATC | AGT | CAG | AAG | TTA | ATC | AAG | GGC | ATT | GAT | 914 |
| Ala | Leu | Ala 285 | Phe | His | Leu | Ile | Ser 290 | Gln | Lys | Leu | Ile | Lys 295 | Gly | Ile | Asp | |
| CCT | CCT | CAC | GTT | CTT | ACT | CCT | GAA | ATG | ATT | CCA | CCA | TCA | GAC | AGG | GCC | 962 |
| Pro | Pro 300 | His | Val | Leu | Thr | Pro | Glu 305 | Met | Ile | Pro | Pro | Ser 310 | Asp | Arg | Ala | |
| AGT | TTA | CAA | AAG | AAC | ATC | ATA | GGA | TCA | AGT | CCT | GTT | GCA | GAT | TTC | TCT | 1010 |
| Ser 315 | Leu | Gln | Lys | Asn | Ile 320 | Ile | Gly | Ser | Ser 325 | Pro | Val | Ala | Asp | Phe | Ser 330 | |
| GCT | ATT | AAG | GAA | CTA | GAT | ACT | CTT | AAC | AAT | GAA | ATA | GTT | GAC | CTA | CAG | 1058 |
| Ala | Ile | Lys | Glu | Leu 335 | Asp | Thr | Leu | Asn | Asn 340 | Glu | Ile | Val | Asp | Leu 345 | Gln | |
| AGG | GAA | AAG | AAT | AAT | GTG | GAA | CAG | GAC | CTT | AAG | GAG | AAG | GAA | GAT | ACT | 1106 |
| Arg | Glu | Lys | Asn 350 | Asn | Val | Glu | Gln | Asp 355 | Leu | Lys | Glu | Lys | Glu 360 | Asp | Thr | |
| ATT | AAA | CAG | AGG | ACA | AGT | GAG | GTT | CAG | GAT | CTT | CAA | GAT | GAA | GTT | CAA | 1154 |
| Ile | Lys | Gln 365 | Arg | Thr | Ser | Glu | Val 370 | Gln | Asp | Leu | Gln | Asp 375 | Glu | Val | Gln | |
| AGG | GAG | AAT | ACT | AAT | CTG | CAA | AAA | CTA | CAG | GCC | CAG | AAA | CAG | CAG | GTA | 1202 |
| Arg | Glu | Asn | Thr 380 | Asn | Leu | Gln | Lys | Leu 385 | Gln | Ala | Gln | Lys | Gln 390 | Gln | Val | |
| CAG | GAA | CTC | CTT | GAT | GAA | CTG | GAT | GAG | CAG | AAA | GCC | CAG | CTG | GAG | GAG | 1250 |
| Gln | Glu 395 | Leu | Leu | Asp | Glu | Leu 400 | Asp | Glu | Gln | Lys | Ala 405 | Gln | Leu | Glu | Glu 410 | |
| CAA | CTC | AAG | GAA | GTC | AGA | AAG | AAA | TGT | GCT | GAG | GAG | GCC | CAA | CTG | ATC | 1298 |
| Gln | Leu | Lys | Glu | Val 415 | Arg | Lys | Lys | Cys | Ala 420 | Glu | Glu | Ala | Gln | Leu 425 | Ile | |
| TCT | TCT | CTG | AAA | GCT | GAA | TTA | ACT | AGT | CAG | GAA | TCG | CAG | ATC | TCC | ACT | 1346 |
| Ser | Ser | Leu | Lys 430 | Ala | Glu | Leu | Thr | Ser 435 | Gln | Glu | Ser | Gln | Ile 440 | Ser | Thr | |
| TAT | GAA | GAA | GAA | TTG | GCA | AAA | GCT | AGA | GAA | GAG | CTG | AGC | CGT | CTA | CAG | 1394 |
| Tyr | Glu | Glu 445 | Glu | Leu | Ala | Lys | Ala 450 | Arg | Glu | Glu | Leu | Ser 455 | Arg | Leu | Gln | |
| CAA | GAA | ACA | GCA | GAA | TTG | GAG | GAG | AGT | GTA | GAG | TCA | GGG | AAG | GCT | CAG | 1442 |
| Gln | Glu | Thr 460 | Ala | Glu | Leu | Glu | Glu 465 | Ser | Val | Glu | Ser | Gly 470 | Lys | Ala | Gln | |
| TTG | GAA | CCT | CTT | CAG | CAG | CAC | CTA | CAA | GAT | TCA | CAA | CAG | GAA | ATT | AGT | 1490 |
| Leu 475 | Glu | Pro | Leu | Gln | Gln 480 | His | Leu | Gln | Asp | Ser 485 | Gln | Gln | Glu | Ile | Ser 490 | |
| TCA | ATG | CAA | ATG | AAA | CTG | ATG | GAA | ATG | AAA | GAT | TTG | GAA | AAT | CAT | AAT | 1538 |
| Ser | Met | Gln | Met | Lys 495 | Leu | Met | Glu | Met | Lys 500 | Asp | Leu | Glu | Asn | His 505 | Asn | |
| AGT | CAG | TTA | AAT | TGG | TGC | AGT | AGC | CCA | CAC | AGC | ATT | CTT | GTA | AAC | GGA | 1586 |
| Ser | Gln | Leu | Asn 510 | Trp | Cys | Ser | Ser | Pro 515 | His | Ser | Ile | Leu | Val 520 | Asn | Gly | |
| GCT | ACA | GAT | TAT | TGC | AGC | CTC | AGC | ACC | AGC | AGT | GAA | ACA | GCC | AAC | | 1634 |
| Ala | Thr | Asp 525 | Tyr | Cys | Ser | Leu | Ser 530 | Thr | Ser | Ser | Glu | Thr 535 | Ala | Asn | | |
| CTT | AAT | GAA | CAT | GTT | GAA | GGC | CAG | AGC | AAC | CTA | GAG | TCT | GAG | CCC | ATA | 1682 |
| Leu | Asn | Glu | His | Val 540 | Glu | Gly | Gln | Ser | Asn 545 | Leu | Glu | Ser | Glu | Pro 550 | Ile | |
| CAC | CAG | GAA | TCT | CCA | GCA | AGA | AGT | AGT | CCT | GAA | CTA | CTG | CCT | TCT | GGT | 1730 |
| His | Gln 555 | Glu | Ser | Pro | Ala | Arg 560 | Ser | Ser | Pro | Glu | Leu 565 | Leu | Pro | Ser | Gly 570 | |
| GTG | ACT | GAT | GAA | AAT | GAG | GTG | ACT | ACA | GCT | GTT | ACT | GAA | AAA | GTT | TGT | 1778 |
| Val | Thr | Asp | Glu | Asn 575 | Glu | Val | Thr | Thr | Ala 580 | Val | Thr | Glu | Lys | Val 585 | Cys | |

```
TCT GAA CTC GAC AAT AAT AGA CAT TCA AAA GAG GAA GAT CCA TTT AAT    1826
Ser Glu Leu Asp Asn Asn Arg His Ser Lys Glu Glu Asp Pro Phe Asn
        590                 595                 600

GTA GAC TCA AGT TCG CTG ACA GGT CCA GTT GCA GAT ACA AAC TTG GAT    1874
Val Asp Ser Ser Ser Leu Thr Gly Pro Val Ala Asp Thr Asn Leu Asp
        605                 610                 615

TTT TTC CAG TCT GAT CCT TTT GTT GGC AGT GAT CCT TTC AAG GAT GAT    1922
Phe Phe Gln Ser Asp Pro Phe Val Gly Ser Asp Pro Phe Lys Asp Asp
620                 625                 630

CCT TTT GGA AAA ATC GAT CCA TTT GGT GGT GAT CCT TTC AAA GGT TCA    1970
Pro Phe Gly Lys Ile Asp Pro Phe Gly Gly Asp Pro Phe Lys Gly Ser
635                 640                 645                 650

GAT CCA TTT GCA TCA GAC TGT TTC TTC AGG CAA TCT ACT GAT CCT TTT    2018
Asp Pro Phe Ala Ser Asp Cys Phe Phe Arg Gln Ser Thr Asp Pro Phe
            655                 660                 665

GCC ACT TCA AGC ACT GAC CCT TTC AGT GCA GCC AAC AAT AGC AGT ATT    2066
Ala Thr Ser Ser Thr Asp Pro Phe Ser Ala Ala Asn Asn Ser Ser Ile
            670                 675                 680

ACA TCG GTA GAA ACG TTG AAG CAC AAT GAT CCT TTT GCT CCT GGT GGA    2114
Thr Ser Val Glu Thr Leu Lys His Asn Asp Pro Phe Ala Pro Gly Gly
            685                 690                 695

ACA GTT GTT GCA GCA AGC GAT TCA GCC ACA GAC CCC TTT GCT TCT GTT    2162
Thr Val Val Ala Ala Ser Asp Ser Ala Thr Asp Pro Phe Ala Ser Val
    700                 705                 710

TTT GGG AAT GAA TCA TTT GGA GGT GGA TTT GCT GAC TTC AGC ACA TTG    2210
Phe Gly Asn Glu Ser Phe Gly Gly Gly Phe Ala Asp Phe Ser Thr Leu
715                 720                 725                 730

TCA AAG GTC AAC AAT GAA GAT CCT TTT CGT TCA GCC ACA TCG AGC TCT    2258
Ser Lys Val Asn Asn Glu Asp Pro Phe Arg Ser Ala Thr Ser Ser Ser
                735                 740                 745

GTC AGC AAC GTA GTG ATT ACA AAA AAT GTA TTT GAG GAA ACA TCG GTC    2306
Val Ser Asn Val Val Ile Thr Lys Asn Val Phe Glu Glu Thr Ser Val
            750                 755                 760

AAA AGT GAA GAT GAA CCC CCA GCA CTG CCA CCA AAG ATC GGA ACT CCA    2354
Lys Ser Glu Asp Glu Pro Pro Ala Leu Pro Pro Lys Ile Gly Thr Pro
        765                 770                 775

ACA AGA CCC TGC CCT CTA CCA CCT GGG AAA AGA TCC ATC AAC AAA TTG    2402
Thr Arg Pro Cys Pro Leu Pro Pro Gly Lys Arg Ser Ile Asn Lys Leu
    780                 785                 790

GAT TCT CCT GAT CCC TTT AAA CTG AAT GAT CCA TTT CAG CCT TTC CCA    2450
Asp Ser Pro Asp Pro Phe Lys Leu Asn Asp Pro Phe Gln Pro Phe Pro
795                 800                 805                 810

GGC AAC GAT AGC CCC AAA GAA AAA GAT CCT GAA ATG TTT TGT GAT CCA    2498
Gly Asn Asp Ser Pro Lys Glu Lys Asp Pro Glu Met Phe Cys Asp Pro
                815                 820                 825

TTC ACT TCT GCT ACT ACC ACT ACC AAT AAA GAG GCT GAT CCA AGC AAT    2546
Phe Thr Ser Ala Thr Thr Thr Thr Asn Lys Glu Ala Asp Pro Ser Asn
            830                 835                 840

TTT GCC AAC TTC AGT GCT TAT CCC TCT GAA GAA GAT ATG ATC GAA TGG    2594
Phe Ala Asn Phe Ser Ala Tyr Pro Ser Glu Glu Asp Met Ile Glu Trp
    845                 850                 855

GCC AAG AGG GAA AGT GAG AGA GAG GAA GAG CAG AGG CTT GCC CGA CTA    2642
Ala Lys Arg Glu Ser Glu Arg Glu Glu Glu Gln Arg Leu Ala Arg Leu
860                 865                 870

AAT CAG CAG GAA CAA GAA GAC TTA GAA CTG GCT ATT GCA CTC AGC AAA    2690
Asn Gln Gln Glu Gln Glu Asp Leu Glu Leu Ala Ile Ala Leu Ser Lys
875                 880                 885                 890

TCT GAG ATA TCA GAA GCA T GAAGAATTCT CTTGTTCTTT GGCAACAATA         2739
Ser Glu Ile Ser Glu Ala
                895
```

```
TAGTATTCTT CTTCCTGAAT ACTGAAACTA TTTACAATGT GTATCAAAAC TACCTGTGAG    2799
CATGGGAATA CAAAAGGTTT GAGATTCCTG TAAATGTGAC AAAATTTTAG GATTTTTTTT    2859
TTTTCTTCAT TACAGATTCG TCTTTTTTTT TTTTTCTTAT AAAAGCCGTA ACCCAGTCAG    2919
ACAAATTCAC CTTCACTTAG GCCCCTGTTC TGGTATACAT TTACTGTGAG CTTTTGCCTG    2979
CCTGTGCTAT TTTACTTGTA AAGCTAGAGC ACCCAAGCTT CTGCCTTCTG GAATATAGAG    3039
AAATAGTTTC ACCCTGCACT ACCCTGTTCT GTAGTTATTC TGATGATAGC CAGTGAGGTT    3099
CTTAAAGTTT GCAGTATTCT CCCCTGATTG GAATGGTTGA GTGAGGGTAA GGGAAAGAAT    3159
ATCTTATTTC TTTTATGATT GGTGCAAATT GGCTAAAGTG CATTTTAAA TTTCCTCTAC     3219
TTAATTTGTT TTTCAGAGAT AAGGAAAAAT ATTTTGCACA GATTACTCC ACTATGGAAA     3279
AGGGATGCTG TAGGTTGAAC CATTATAGCC TCAGATTCGA TCTTTTCCTA ACTAAAAATA    3339
TTAAAGCCTC ATGTGTGAAA TAAATTTTA AAAAGATTTA TCTGGATTTA GAGAATTTTA     3399
GATCAACAGA TACCTCTCAG TGTGTTTGCT AATTAATAAA AATCAGTTTC TTACAAATAA    3459
AGTTTGTAAG AAAATGTTCA TTTTAAGTGA TAGATAGTGG AGAAATTTA TCACCTAAAA     3519
TATACCCATC AGTATAAGGC AAGCAAAAGT CTTAACATGG CAGCCATTCT GCCTTTGCCG    3579
TGGCCCTGTC CTGTTTAGTT CTTAGTGGGT TAATTTTTGT ACTTTTGCAG AAGAAACTTC    3639
AGCAAGCTAG AACTGGAAGG TACTTTAATT TTTCATATAT ATTTGTTTTT TTTTTTTTAA    3699
TGAAGGCTCA TTTACTTGAA ATGTAAAAAC TTTCACTGAA TACAAATAGA AAAAGTGATG    3759
TGTTTTATAT CATATTGCTT TTTGTCCATC TTTGTGGTTT AGTTTATTTA CTCACTTCAT    3819
GTTTTTCACC TATAAAATTG TCAAGCTAGC AAAAAAACTC TTGTTTTTTT AATTGGGAGA    3879
GAAGAGACCT GCCAGATTAT CAGACCTCTT CATGTTAAAA GACCATCTCC TGTAAAACTG    3939
ACCTAGTGGA CAAGCTGAAT TTGAAATAGA CTGTGAAGTA AGCTGTAACT TGTCATTTTA    3999
ATTTTGTTTA ACACGGTTAC TGACTTAGAT GATGTATTAA ATACCAAGAT AAAGAAAAAT    4059
GCACCTAAAA TCTAATTAGA ATTCTCTGGG TCACCAAGTC AAGGTGGTAT TGATCTGTGT    4119
TAATCTGAGT AACTTATTGC CTAGCCTATA AATAAATTCC AATATC                   4165
```

( 2 ) INFORMATION FOR SEQ ID NO:2:

( i ) SEQUENCE CHARACTERISTICS:
        ( A ) LENGTH: 896 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Ala Ala Ala Gln Leu Ser Leu Thr Gln Leu Ser Ser Gly Asn
 1               5                  10                  15

Pro Val Tyr Glu Lys Tyr Tyr Arg Gln Val Asp Thr Gly Asn Thr Gly
             20                  25                  30

Arg Val Leu Ala Ser Asp Ala Ala Ala Phe Leu Lys Lys Ser Gly Leu
         35                  40                  45

Pro Asp Leu Ile Leu Gly Lys Ile Trp Asp Leu Ala Asp Thr Asp Gly
     50                  55                  60

Lys Gly Ile Leu Asn Lys Gln Glu Phe Phe Val Ala Leu Arg Leu Val
 65                  70                  75                  80

Ala Cys Ala Gln Asn Gly Leu Glu Val Ser Leu Ser Ser Leu Asn Leu
                 85                  90                  95

Ala Val Pro Pro Pro Arg Phe His Asp Thr Ser Ser Pro Leu Leu Ile
```

|  |  |  |  |  | 100 |  |  |  |  | 105 |  |  |  |  | 110 |  |
|---|---|---|---|---|---|---|---|---|---|---|---|---|---|---|---|---|---|

Ser Gly Thr Ser Ala Ala Glu Leu Pro Trp Ala Val Lys Pro Glu Asp
          115                       120                       125

Lys Ala Lys Tyr Asp Ala Ile Phe Asp Ser Leu Ser Pro Val Asn Gly
130                     135                   140

Phe Leu Ser Gly Asp Lys Val Lys Pro Val Leu Leu Asn Ser Lys Leu
145                   150               155                   160

Pro Val Asp Ile Leu Gly Arg Val Trp Glu Leu Ser Asp Ile Asp His
                   165              170                   175

Asp Gly Met Leu Asp Arg Asp Glu Phe Ala Val Ala Met Phe Leu Val
        180                     185               190

Tyr Cys Ala Leu Glu Lys Glu Pro Val Pro Met Ser Leu Pro Pro Ala
       195              200               205

Leu Val Pro Pro Ser Lys Arg Lys Thr Trp Val Val Ser Pro Ala Glu
   210                 215               220

Lys Ala Lys Tyr Asp Glu Ile Phe Leu Lys Thr Asp Lys Asp Met Asp
225                 230              235               240

Gly Phe Val Ser Gly Leu Glu Val Arg Glu Ile Phe Leu Lys Thr Gly
         245             250               255

Leu Pro Ser Thr Leu Leu Ala His Ile Trp Ser Leu Cys Asp Thr Lys
       260              265               270

Asp Cys Gly Lys Leu Ser Lys Asp Gln Phe Ala Leu Ala Phe His Leu
       275              280               285

Ile Ser Gln Lys Leu Ile Lys Gly Ile Asp Pro Pro His Val Leu Thr
   290                 295               300

Pro Glu Met Ile Pro Pro Ser Asp Arg Ala Ser Leu Gln Lys Asn Ile
305                 310              315               320

Ile Gly Ser Ser Pro Val Ala Asp Phe Ser Ala Ile Lys Glu Leu Asp
            325               330               335

Thr Leu Asn Asn Glu Ile Val Asp Leu Gln Arg Glu Lys Asn Asn Val
       340              345               350

Glu Gln Asp Leu Lys Glu Lys Glu Asp Thr Ile Lys Gln Arg Thr Ser
       355              360               365

Glu Val Gln Asp Leu Gln Asp Glu Val Gln Arg Glu Asn Thr Asn Leu
   370                 375               380

Gln Lys Leu Gln Ala Gln Lys Gln Gln Val Gln Glu Leu Leu Asp Glu
385                 390              395               400

Leu Asp Glu Gln Lys Ala Gln Leu Glu Gln Leu Lys Glu Val Arg
            405               410               415

Lys Lys Cys Ala Glu Glu Ala Gln Leu Ile Ser Ser Leu Lys Ala Glu
            420               425               430

Leu Thr Ser Gln Glu Ser Gln Ile Ser Thr Tyr Glu Glu Leu Ala
       435              440               445

Lys Ala Arg Glu Glu Leu Ser Arg Leu Gln Gln Glu Thr Ala Glu Leu
   450                 455               460

Glu Glu Ser Val Glu Ser Gly Lys Ala Gln Leu Glu Pro Leu Gln Gln
465                 470              475               480

His Leu Gln Asp Ser Gln Gln Glu Ile Ser Ser Met Gln Met Lys Leu
            485               490               495

Met Glu Met Lys Asp Leu Glu Asn His Asn Ser Gln Leu Asn Trp Cys
          500               505               510

Ser Ser Pro His Ser Ile Leu Val Asn Gly Ala Thr Asp Tyr Cys Ser
       515              520               525

| | | | | | | | | | | | | | |
|---|---|---|---|---|---|---|---|---|---|---|---|---|---|
| Leu | Ser 530 | Thr | Ser | Ser | Ser | Glu 535 | Thr | Ala | Asn | Leu 540 | Asn | His | Val | Glu |
| Gly 545 | Gln | Ser | Asn | Leu | Glu 550 | Ser | Glu | Pro | Ile | His 555 | Gln | Glu | Ser | Pro | Ala 560 |
| Arg | Ser | Ser | Pro | Glu 565 | Leu | Leu | Pro | Ser | Gly 570 | Val | Thr | Asp | Glu | Asn 575 | Glu |
| Val | Thr | Thr | Ala 580 | Val | Thr | Glu | Lys | Val 585 | Cys | Ser | Glu | Leu | Asp 590 | Asn | Asn |
| Arg | His | Ser 595 | Lys | Glu | Glu | Asp | Pro 600 | Phe | Asn | Val | Asp | Ser 605 | Ser | Ser | Leu |
| Thr | Gly 610 | Pro | Val | Ala | Asp | Thr 615 | Asn | Leu | Asp | Phe | Phe 620 | Gln | Ser | Asp | Pro |
| Phe 625 | Val | Gly | Ser | Asp | Pro 630 | Phe | Lys | Asp | Asp | Pro 635 | Phe | Gly | Lys | Ile | Asp 640 |
| Pro | Phe | Gly | Gly | Asp 645 | Pro | Phe | Lys | Gly | Ser 650 | Asp | Pro | Phe | Ala | Ser 655 | Asp |
| Cys | Phe | Phe | Arg 660 | Gln | Ser | Thr | Asp | Pro 665 | Phe | Ala | Thr | Ser | Ser 670 | Thr | Asp |
| Pro | Phe | Ser 675 | Ala | Ala | Asn | Asn | Ser 680 | Ser | Ile | Thr | Ser | Val 685 | Glu | Thr | Leu |
| Lys | His 690 | Asn | Asp | Pro | Phe | Ala 695 | Pro | Gly | Gly | Thr | Val 700 | Val | Ala | Ala | Ser |
| Asp 705 | Ser | Ala | Thr | Asp | Pro 710 | Phe | Ala | Ser | Val | Phe 715 | Gly | Asn | Glu | Ser | Phe 720 |
| Gly | Gly | Gly | Phe | Ala 725 | Asp | Phe | Ser | Thr | Leu 730 | Ser | Lys | Val | Asn | Asn 735 | Glu |
| Asp | Pro | Phe | Arg 740 | Ser | Ala | Thr | Ser | Ser 745 | Ser | Val | Ser | Asn | Val 750 | Val | Ile |
| Thr | Lys | Asn 755 | Val | Phe | Glu | Glu | Thr 760 | Ser | Val | Lys | Ser | Glu 765 | Asp | Glu | Pro |
| Pro | Ala 770 | Leu | Pro | Pro | Lys | Ile 775 | Gly | Thr | Pro | Thr | Arg 780 | Pro | Cys | Pro | Leu |
| Pro 785 | Pro | Gly | Lys | Arg | Ser 790 | Ile | Asn | Lys | Leu | Asp 795 | Ser | Pro | Asp | Pro 800 |
| Lys | Leu | Asn | Asp | Pro 805 | Phe | Gln | Pro | Phe | Pro 810 | Gly | Asn | Asp | Ser | Pro 815 | Lys |
| Glu | Lys | Asp | Pro 820 | Glu | Met | Phe | Cys | Asp 825 | Pro | Phe | Thr | Ser | Ala 830 | Thr | Thr |
| Thr | Thr | Asn 835 | Lys | Glu | Ala | Asp | Pro 840 | Ser | Asn | Phe | Ala | Asn 845 | Phe | Ser | Ala |
| Tyr | Pro 850 | Ser | Glu | Glu | Asp | Met 855 | Ile | Glu | Trp | Ala | Lys 860 | Arg | Glu | Ser | Glu |
| Arg 865 | Glu | Glu | Glu | Gln | Arg 870 | Leu | Ala | Arg | Leu | Asn 875 | Gln | Gln | Glu | Gln 880 |
| Asp | Leu | Glu | Leu | Ala 885 | Ile | Ala | Leu | Ser | Lys 890 | Ser | Glu | Ile | Ser | Glu 895 | Ala |

( 2 ) INFORMATION FOR SEQ ID NO:3:

( i ) SEQUENCE CHARACTERISTICS:
( A ) LENGTH: 3033 base pairs
( B ) TYPE: nucleic acid
( C ) STRANDEDNESS: double
( D ) TOPOLOGY: linear ( i i ) MOLECULE TYPE: cDNA (iii) HYPOTHETICAL: NO (iv) ANTI-SENSE: NO (ix) FEATURE:
    (A) NAME/KEY: CDS
    (B) LOCATION: 111..2802

(xi) SEQUENCE DESCRIPTION: SEQ ID NO:3:

```
CCGAGACGCC CGGCGCCGGC CTCGCCTACG GCCTGTCCCT CCGCCTCCTT CCCGCCCCGG          60

GCCCCCGTCC GTCCGTCCTT CCTTCCCCTC CCGTGCATGA TGGAAACACC ATG GCT           116
                                                        Met Ala
                                                          1

GCG GCA GCC CAG CTC TCC CTG ACA CAG TTG TCA AGT GGG AAT CCT GTA          164
Ala Ala Ala Gln Leu Ser Leu Thr Gln Leu Ser Ser Gly Asn Pro Val
          5               10                  15

TAT GAA AAA TAC TAC AGA CAG GTT GAG GCA GGC AAT ACT GGA AGG GTG          212
Tyr Glu Lys Tyr Tyr Arg Gln Val Glu Ala Gly Asn Thr Gly Arg Val
     20              25                  30

TTG GCG TTA GAT GCT GCT GCA TTC CTG AAA AAG TCA GGG CTT CCA GAC          260
Leu Ala Leu Asp Ala Ala Ala Phe Leu Lys Lys Ser Gly Leu Pro Asp
 35              40              45                  50

TTG ATT CTT GGA AAG ATT TGG GAT TTA GCT GAC ACA GAT GGC AAA GGT          308
Leu Ile Leu Gly Lys Ile Trp Asp Leu Ala Asp Thr Asp Gly Lys Gly
                 55              60                  65

GTC CTG AGC AAA CAA GAA TTC TTT GTT GCT TTA CGG CTT GTG GCA TGT          356
Val Leu Ser Lys Gln Glu Phe Phe Val Ala Leu Arg Leu Val Ala Cys
             70              75                  80

GCT CAG AAT GGA CTG GAA GTT TCA CTG AGT AGC CTA AGT CTG GCT GTT          404
Ala Gln Asn Gly Leu Glu Val Ser Leu Ser Ser Leu Ser Leu Ala Val
             85              90                  95

CCT CCA CCA AGA TTT CAT GAC TCC AGC AGT CCG TTG CTA ACC AGT GGG          452
Pro Pro Pro Arg Phe His Asp Ser Ser Ser Pro Leu Leu Thr Ser Gly
        100             105             110

CCC TCA GTT GCT GAG CTC CCG TGG GCT GTA AAG TCT GAA GAT AAA GCC          500
Pro Ser Val Ala Glu Leu Pro Trp Ala Val Lys Ser Glu Asp Lys Ala
115             120             125                 130

AAA TAT GAT GCA ATT TTT GAC AGT TTA AGC CCA GTG GAT GGA TTT TTG          548
Lys Tyr Asp Ala Ile Phe Asp Ser Leu Ser Pro Val Asp Gly Phe Leu
                135             140                 145

TCT GGT GAT AAA GTG AAA CCA GTG TTG CTC AAC TCT AAG TTA CCT GTG          596
Ser Gly Asp Lys Val Lys Pro Val Leu Leu Asn Ser Lys Leu Pro Val
            150             155                 160

GAA ATC CTT GGA AGA GTT TGG GAG TTG AGT GAT ATT GAC CAC GAT GGA          644
Glu Ile Leu Gly Arg Val Trp Glu Leu Ser Asp Ile Asp His Asp Gly
        165             170                 175

AAG CTG GAC AGA GAT GAG TTT GCA GTT GCC ATG TTT TTG GTA TAC TGT          692
Lys Leu Asp Arg Asp Glu Phe Ala Val Ala Met Phe Leu Val Tyr Cys
        180             185                 190

GCA CTG GAG AAA GAA CCT GTG CCA ATG TCC TTG CCT CCA GCC TTG GTG          740
Ala Leu Glu Lys Glu Pro Val Pro Met Ser Leu Pro Pro Ala Leu Val
195             200             205                 210

CCA CCT TCT AAG AGA AAA ACG TGG GTT GTA TCC CCT GCA GAA AAA GCT          788
Pro Pro Ser Lys Arg Lys Thr Trp Val Val Ser Pro Ala Glu Lys Ala
                215             220                 225

AAA TAT GAT GAA ATT TTT CTG AAA ACT GAT AAG GAT ATG GAT GGA TAT          836
Lys Tyr Asp Glu Ile Phe Leu Lys Thr Asp Lys Asp Met Asp Gly Tyr
                230             235                 240

GTG TCT GGA CTG GAG GTC CGT GAA ACC TTC CTG AAA ACA GGT TTA CCT          884
Val Ser Gly Leu Glu Val Arg Glu Thr Phe Leu Lys Thr Gly Leu Pro
            245             250                 255
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| TCT | GCC | TTG | CTA | GCC | CAC | ATT | TGG | TCA | CTA | TGT | GAC | ACA | AAG | GGC | TGT | 932  |
| Ser | Ala | Leu | Leu | Ala | His | Ile | Trp | Ser | Leu | Cys | Asp | Thr | Lys | Gly | Cys |      |
| 260 |     |     |     |     | 265 |     |     |     |     | 270 |     |     |     |     |     |      |
| GGG | AAG | CTT | TCA | AAA | GAC | CAG | TTT | GCC | TTG | GCT | TTT | CAC | TTA | ATC | AAT | 980  |
| Gly | Lys | Leu | Ser | Lys | Asp | Gln | Phe | Ala | Leu | Ala | Phe | His | Leu | Ile | Asn |      |
| 275 |     |     |     | 280 |     |     |     |     | 285 |     |     |     |     |     | 290 |      |
| CAG | AAG | TTA | ATA | AAA | GGC | ATT | GAC | CCT | CCT | CAT | AGT | CTC | ACT | CCT | GAG | 1028 |
| Gln | Lys | Leu | Ile | Lys | Gly | Ile | Asp | Pro | Pro | His | Ser | Leu | Thr | Pro | Glu |      |
|     |     |     |     | 295 |     |     |     |     | 300 |     |     |     |     | 305 |     |      |
| ATG | ATT | CCA | CCA | TCA | GAC | AGA | TCC | AGT | TTA | CAA | AAG | AAC | ATC | ACA | GGA | 1076 |
| Met | Ile | Pro | Pro | Ser | Asp | Arg | Ser | Ser | Leu | Gln | Lys | Asn | Ile | Thr | Gly |      |
|     |     |     | 310 |     |     |     |     | 315 |     |     |     |     | 320 |     |     |      |
| TCA | AGT | CCT | GTT | GCA | GAT | TTT | TCT | GCT | ATT | AAG | GAA | CTA | GAT | ACC | CTT | 1124 |
| Ser | Ser | Pro | Val | Ala | Asp | Phe | Ser | Ala | Ile | Lys | Glu | Leu | Asp | Thr | Leu |      |
|     |     | 325 |     |     |     |     | 330 |     |     |     |     | 335 |     |     |     |      |
| AAC | AAT | GAA | ATA | GTT | GAC | CTG | CAG | AGG | GAA | AAG | AAC | AAT | GTG | GAG | CAG | 1172 |
| Asn | Asn | Glu | Ile | Val | Asp | Leu | Gln | Arg | Glu | Lys | Asn | Asn | Val | Glu | Gln |      |
|     | 340 |     |     |     |     | 345 |     |     |     |     | 350 |     |     |     |     |      |
| GAC | CTT | AAA | GAG | AAG | GAA | GAC | ACA | GTT | AAG | CAG | AGG | ACC | AGT | GAG | GTT | 1220 |
| Asp | Leu | Lys | Glu | Lys | Glu | Asp | Thr | Val | Lys | Gln | Arg | Thr | Ser | Glu | Val |      |
| 355 |     |     |     |     | 360 |     |     |     |     | 365 |     |     |     |     | 370 |      |
| CAG | GAT | CTT | CAA | GAT | GAA | GTT | CAA | AGG | GAG | AGT | ATT | AAT | CTA | CAA | AAA | 1268 |
| Gln | Asp | Leu | Gln | Asp | Glu | Val | Gln | Arg | Glu | Ser | Ile | Asn | Leu | Gln | Lys |      |
|     |     |     |     | 375 |     |     |     |     | 380 |     |     |     |     | 385 |     |      |
| CTG | CAG | GCC | CAG | AAG | CAG | CAG | GTG | CAG | GAG | CTC | CTG | GGT | GAA | CTG | GAT | 1316 |
| Leu | Gln | Ala | Gln | Lys | Gln | Gln | Val | Gln | Glu | Leu | Leu | Gly | Glu | Leu | Asp |      |
|     |     |     | 390 |     |     |     |     | 395 |     |     |     |     | 400 |     |     |      |
| GAG | CAG | AAA | GCC | CAG | CTG | GAG | GAG | CAG | CTC | CAG | GAA | GTC | AGG | AAA | AAG | 1364 |
| Glu | Gln | Lys | Ala | Gln | Leu | Glu | Glu | Gln | Leu | Gln | Glu | Val | Arg | Lys | Lys |      |
|     |     | 405 |     |     |     |     | 410 |     |     |     |     | 415 |     |     |     |      |
| TGT | GCT | GAG | GAG | GCC | CAG | CTG | ATT | TCT | TCC | CTG | AAA | GCA | GAA | ATA | ACT | 1412 |
| Cys | Ala | Glu | Glu | Ala | Gln | Leu | Ile | Ser | Ser | Leu | Lys | Ala | Glu | Ile | Thr |      |
|     | 420 |     |     |     |     | 425 |     |     |     |     | 430 |     |     |     |     |      |
| AGT | CAA | GAA | TCT | CAG | ATC | TCC | AGT | TAT | GAG | GAA | GAA | CTG | TTG | AAA | GCT | 1460 |
| Ser | Gln | Glu | Ser | Gln | Ile | Ser | Ser | Tyr | Glu | Glu | Glu | Leu | Leu | Lys | Ala |      |
| 435 |     |     |     |     | 440 |     |     |     |     | 445 |     |     |     |     | 450 |      |
| AGA | GAA | GAA | CTA | AGT | CGC | CTA | CAA | CAA | GAA | ACA | GCA | CAA | TTG | GAA | GAA | 1508 |
| Arg | Glu | Glu | Leu | Ser | Arg | Leu | Gln | Gln | Glu | Thr | Ala | Gln | Leu | Glu | Glu |      |
|     |     |     |     | 455 |     |     |     |     | 460 |     |     |     |     | 465 |     |      |
| AGT | GTG | GAG | TCA | GGG | AAG | GCT | CAG | CTG | GAA | CCT | CTT | CAG | CAG | CAC | CTA | 1556 |
| Ser | Val | Glu | Ser | Gly | Lys | Ala | Gln | Leu | Glu | Pro | Leu | Gln | Gln | His | Leu |      |
|     |     |     | 470 |     |     |     |     | 475 |     |     |     |     | 480 |     |     |      |
| CAA | GAG | TCA | CAA | CAG | GAA | ATC | AGC | TCA | ATG | CAA | ATG | AGA | TTG | GAA | ATG | 1604 |
| Gln | Glu | Ser | Gln | Gln | Glu | Ile | Ser | Ser | Met | Gln | Met | Arg | Leu | Glu | Met |      |
|     |     | 485 |     |     |     |     | 490 |     |     |     |     | 495 |     |     |     |      |
| AAA | GAT | CTG | GAA | ACT | GAT | AAT | AAC | CAA | TCA | AAT | TGG | AGC | AGT | AGC | CCA | 1652 |
| Lys | Asp | Leu | Glu | Thr | Asp | Asn | Asn | Gln | Ser | Asn | Trp | Ser | Ser | Ser | Pro |      |
|     |     | 500 |     |     |     |     | 505 |     |     |     |     | 510 |     |     |     |      |
| CAA | AGC | GTT | CTT | GTT | AAT | GGT | GCT | ACA | GAT | TAC | TGT | AGC | CTC | AGC | ACC | 1700 |
| Gln | Ser | Val | Leu | Val | Asn | Gly | Ala | Thr | Asp | Tyr | Cys | Ser | Leu | Ser | Thr |      |
| 515 |     |     |     |     | 520 |     |     |     |     | 525 |     |     |     |     | 530 |      |
| AGC | AGC | AGT | GAA | ACA | GCC | AAC | TTC | AAC | GAA | CAT | GCT | GAA | GGC | CAA | AAC | 1748 |
| Ser | Ser | Ser | Glu | Thr | Ala | Asn | Phe | Asn | Glu | His | Ala | Glu | Gly | Gln | Asn |      |
|     |     |     |     | 535 |     |     |     |     | 540 |     |     |     |     | 545 |     |      |
| AAC | CTA | GAG | TCT | GAA | CCC | ACA | CAC | CAG | GAG | TCC | TCA | GTA | AGA | AGT | AGT | 1796 |
| Asn | Leu | Glu | Ser | Glu | Pro | Thr | His | Gln | Glu | Ser | Ser | Val | Arg | Ser | Ser |      |
|     |     |     | 550 |     |     |     |     | 555 |     |     |     |     | 560 |     |     |      |
| CCT | GAA | ATC | GCA | CCT | TCT | GAT | GTG | ACT | GAT | GAA | AGT | GAG | GCT | GTG | ACT | 1844 |
| Pro | Glu | Ile | Ala | Pro | Ser | Asp | Val | Thr | Asp | Glu | Ser | Glu | Ala | Val | Thr |      |
|     |     | 565 |     |     |     |     | 570 |     |     |     |     | 575 |     |     |     |      |

| | | | | | | | | | | | | | | | | |
|---|---|---|---|---|---|---|---|---|---|---|---|---|---|---|---|---|
| GTG | GCT | GGT | AAT | GAG | AAA | GTT | ACT | CCG | AGA | TTT | GAC | GAT | GAC | AAG | CAC | 1892 |
| Val | Ala | Gly | Asn | Glu | Lys | Val | Thr | Pro | Arg | Phe | Asp | Asp | Asp | Lys | His | |
| | 580 | | | | 585 | | | | | 590 | | | | | | |
| TCA | AAA | GAG | GAA | GAT | CCA | TTT | AAT | GTA | GAA | TCA | AGT | TCA | CTG | ACA | GAT | 1940 |
| Ser | Lys | Glu | Glu | Asp | Pro | Phe | Asn | Val | Glu | Ser | Ser | Ser | Leu | Thr | Asp | |
| 595 | | | | | 600 | | | | | 605 | | | | | 610 | |
| GCA | GTT | GCA | GAT | ACA | AAC | TTG | GAT | TTT | TTC | CAG | TCT | GAT | CCT | TTT | GTT | 1988 |
| Ala | Val | Ala | Asp | Thr | Asn | Leu | Asp | Phe | Phe | Gln | Ser | Asp | Pro | Phe | Val | |
| | | | | 615 | | | | | 620 | | | | | 625 | | |
| GGC | AGT | GAT | CCT | TTC | AAG | GAT | GAT | CCT | TTT | GGA | AAA | ATT | GAT | CCA | TTT | 2036 |
| Gly | Ser | Asp | Pro | Phe | Lys | Asp | Asp | Pro | Phe | Gly | Lys | Ile | Asp | Pro | Phe | |
| | | | 630 | | | | | 635 | | | | | 640 | | | |
| GGT | GGT | GAC | CCT | TTC | AAA | GGC | TCA | GAT | CCT | TTT | GCG | TCT | GAT | TGC | TTC | 2084 |
| Gly | Gly | Asp | Pro | Phe | Lys | Gly | Ser | Asp | Pro | Phe | Ala | Ser | Asp | Cys | Phe | |
| | | 645 | | | | | 650 | | | | | 655 | | | | |
| TTT | AAG | CAG | ACT | TCT | ACT | GAT | CCT | TTT | ACC | ACT | TCA | AGT | ACG | GAC | CCT | 2132 |
| Phe | Lys | Gln | Thr | Ser | Thr | Asp | Pro | Phe | Thr | Thr | Ser | Ser | Thr | Asp | Pro | |
| | 660 | | | | | 665 | | | | | 670 | | | | | |
| TTC | AGT | GCA | TCC | AGC | AAC | AGC | AGT | AAT | ACA | TCG | GTA | GAA | ACT | TGG | AAG | 2180 |
| Phe | Ser | Ala | Ser | Ser | Asn | Ser | Ser | Asn | Thr | Ser | Val | Glu | Thr | Trp | Lys | |
| 675 | | | | | 680 | | | | | 685 | | | | | 690 | |
| CAC | AAT | GAC | CCA | TTT | GCT | CCT | GGT | GGA | ACA | GTT | GTT | GCT | GCA | GCG | AGT | 2228 |
| His | Asn | Asp | Pro | Phe | Ala | Pro | Gly | Gly | Thr | Val | Val | Ala | Ala | Ala | Ser | |
| | | | | 695 | | | | | 700 | | | | | 705 | | |
| GAT | TCA | GCC | ACA | GAC | CCT | TTT | GCT | TCT | GTT | TTC | GGA | AAT | GAA | TCA | TTT | 2276 |
| Asp | Ser | Ala | Thr | Asp | Pro | Phe | Ala | Ser | Val | Phe | Gly | Asn | Glu | Ser | Phe | |
| | | | 710 | | | | | 715 | | | | | 720 | | | |
| GGA | GAT | GGA | TTT | GCT | GAC | TTC | AGC | ACA | TTA | TCA | AAG | GTC | AAC | AAT | GAA | 2324 |
| Gly | Asp | Gly | Phe | Ala | Asp | Phe | Ser | Thr | Leu | Ser | Lys | Val | Asn | Asn | Glu | |
| | | 725 | | | | | 730 | | | | | 735 | | | | |
| GAT | GCT | TTT | AAT | CCT | ACC | ATA | TCA | AGT | TCT | ACC | AGC | AGT | GTG | ACC | ATT | 2372 |
| Asp | Ala | Phe | Asn | Pro | Thr | Ile | Ser | Ser | Ser | Thr | Ser | Ser | Val | Thr | Ile | |
| | 740 | | | | | 745 | | | | | 750 | | | | | |
| GCA | AAA | CCT | ATG | TTA | GAG | GAA | ACA | GCC | AGC | AAG | AGT | GAA | GAT | GTG | CCT | 2420 |
| Ala | Lys | Pro | Met | Leu | Glu | Glu | Thr | Ala | Ser | Lys | Ser | Glu | Asp | Val | Pro | |
| 755 | | | | | 760 | | | | | 765 | | | | | 770 | |
| CCA | GCA | CTG | CCG | CCC | AAA | GTT | GGC | ACT | CCA | ACA | AGA | CCT | TGC | CCG | CCA | 2468 |
| Pro | Ala | Leu | Pro | Pro | Lys | Val | Gly | Thr | Pro | Thr | Arg | Pro | Cys | Pro | Pro | |
| | | | | 775 | | | | | 780 | | | | | 785 | | |
| CCC | CCT | GGG | AAA | AGA | CCC | ATC | AAC | AAA | TTG | GAT | TCT | TCT | GAT | CCC | CTT | 2516 |
| Pro | Pro | Gly | Lys | Arg | Pro | Ile | Asn | Lys | Leu | Asp | Ser | Ser | Asp | Pro | Leu | |
| | | | 790 | | | | | 795 | | | | | 800 | | | |
| AAA | CTG | AAT | GAT | CCA | TTT | CAG | CCT | TTC | CCA | GGC | AAT | GAT | AGT | CCC | AAA | 2564 |
| Lys | Leu | Asn | Asp | Pro | Phe | Gln | Pro | Phe | Pro | Gly | Asn | Asp | Ser | Pro | Lys | |
| | | | 805 | | | | | 810 | | | | | 815 | | | |
| GAA | AAA | GAT | CCT | GAT | ATG | TTT | TGT | GAT | CCA | TTC | ACT | TCT | TCT | ACC | ACT | 2612 |
| Glu | Lys | Asp | Pro | Asp | Met | Phe | Cys | Asp | Pro | Phe | Thr | Ser | Ser | Thr | Thr | |
| | 820 | | | | | 825 | | | | | 830 | | | | | |
| ACC | AAT | AAA | GAG | GCT | GAC | CCA | AGC | AAT | TTT | GCT | AAC | TTC | AGT | GCT | TAT | 2660 |
| Thr | Asn | Lys | Glu | Ala | Asp | Pro | Ser | Asn | Phe | Ala | Asn | Phe | Ser | Ala | Tyr | |
| 835 | | | | | 840 | | | | | 845 | | | | | 850 | |
| CCC | TCT | GAA | GAA | GAT | ATG | ATT | GAA | TGG | GCA | AAA | AGG | GAA | AGT | GAG | CGG | 2708 |
| Pro | Ser | Glu | Glu | Asp | Met | Ile | Glu | Trp | Ala | Lys | Arg | Glu | Ser | Glu | Arg | |
| | | | | 855 | | | | | 860 | | | | | 865 | | |
| GAA | GAA | GAA | CAG | AGG | CTT | GCC | AGA | CTA | AAT | CAG | CAG | GAG | CAA | GAA | GAC | 2756 |
| Glu | Glu | Glu | Gln | Arg | Leu | Ala | Arg | Leu | Asn | Gln | Gln | Glu | Gln | Glu | Asp | |
| | | | 870 | | | | | 875 | | | | | 880 | | | |
| TTG | GAA | CTG | GCC | ATT | GCA | CTT | AGC | AAA | TCT | GAG | ATC | TCA | GAA | GCA | T | 2802 |
| Leu | Glu | Leu | Ala | Ile | Ala | Leu | Ser | Lys | Ser | Glu | Ile | Ser | Glu | Ala | | |
| | 885 | | | | | 890 | | | | | 895 | | | | | |

```
GAAGAGTTAT CTGTCCTTTG TCAGCAGTAC AGTGCTCTCT GGAACACTGA AGCTATTTAC    2862

CATGTGCATC AAACTACCTA TGAGCATGGG ATACAAAGG  TTTGAGATTC CTAGAAATGT    2922

GACAAAAGTC TAGTTTGTTT TTTTTTTTTT TTTTGGGGGG GGGTGCTATT TCAAATGTGT    2982

CTTTTATTTT TTCTTCCAAA AGCAGTACCC TAATTAAACG GCTTTGCCTA G              3033
```

( 2 ) INFORMATION FOR SEQ ID NO:4:

( i ) SEQUENCE CHARACTERISTICS:
        ( A ) LENGTH: 897 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ala Ala Ala Ala Gln Leu Ser Leu Thr Gln Leu Ser Ser Gly Asn
 1               5                  10                  15

Pro Val Tyr Glu Lys Tyr Tyr Arg Gln Val Glu Ala Gly Asn Thr Gly
            20                  25                  30

Arg Val Leu Ala Leu Asp Ala Ala Phe Leu Lys Lys Ser Gly Leu
        35                  40                  45

Pro Asp Leu Ile Leu Gly Lys Ile Trp Asp Leu Ala Asp Thr Asp Gly
    50                  55                  60

Lys Gly Val Leu Ser Lys Gln Glu Phe Phe Val Ala Leu Arg Leu Val
65                  70                  75                  80

Ala Cys Ala Gln Asn Gly Leu Glu Val Ser Leu Ser Ser Leu Ser Leu
                85                  90                  95

Ala Val Pro Pro Pro Arg Phe His Asp Ser Ser Pro Leu Leu Thr
                100             105                 110

Ser Gly Pro Ser Val Ala Glu Leu Pro Trp Ala Val Lys Ser Glu Asp
            115                 120                 125

Lys Ala Lys Tyr Asp Ala Ile Phe Asp Ser Leu Ser Pro Val Asp Gly
    130                 135                 140

Phe Leu Ser Gly Asp Lys Val Lys Pro Val Leu Leu Asn Ser Lys Leu
145                 150                 155                 160

Pro Val Glu Ile Leu Gly Arg Val Trp Glu Leu Ser Asp Ile Asp His
                165                 170                 175

Asp Gly Lys Leu Asp Arg Asp Glu Phe Ala Val Ala Met Phe Leu Val
            180                 185                 190

Tyr Cys Ala Leu Glu Lys Glu Pro Val Pro Met Ser Leu Pro Pro Ala
        195                 200                 205

Leu Val Pro Pro Ser Lys Arg Lys Thr Trp Val Val Ser Pro Ala Glu
    210                 215                 220

Lys Ala Lys Tyr Asp Glu Ile Phe Leu Lys Thr Asp Lys Asp Met Asp
225                 230                 235                 240

Gly Tyr Val Ser Gly Leu Glu Val Arg Glu Thr Phe Leu Lys Thr Gly
                245                 250                 255

Leu Pro Ser Ala Leu Leu Ala His Ile Trp Ser Leu Cys Asp Thr Lys
            260                 265                 270

Gly Cys Gly Lys Leu Ser Lys Asp Gln Phe Ala Leu Ala Phe His Leu
        275                 280                 285

Ile Asn Gln Lys Leu Ile Lys Gly Ile Asp Pro Pro His Ser Leu Thr
    290                 295                 300

Pro Glu Met Ile Pro Pro Ser Asp Arg Ser Ser Leu Gln Lys Asn Ile
305                 310                 315                 320
```

Thr Gly Ser Ser Pro Val Ala Asp Phe Ser Ala Ile Lys Glu Leu Asp
            325                 330                335

Thr Leu Asn Asn Glu Ile Val Asp Leu Gln Arg Glu Lys Asn Asn Val
        340                 345                 350

Glu Gln Asp Leu Lys Glu Lys Asp Thr Val Lys Arg Thr Ser
        355             360             365

Glu Val Gln Asp Leu Gln Asp Glu Val Gln Arg Glu Ser Ile Asn Leu
370                 375                 380

Gln Lys Leu Gln Ala Gln Lys Gln Val Gln Glu Leu Leu Gly Glu
385             390             395                 400

Leu Asp Glu Gln Lys Ala Gln Leu Glu Gln Leu Gln Glu Val Arg
            405             410                 415

Lys Lys Cys Ala Glu Glu Ala Gln Leu Ile Ser Ser Leu Lys Ala Glu
            420                 425             430

Ile Thr Ser Gln Glu Ser Gln Ile Ser Ser Tyr Glu Glu Glu Leu Leu
        435             440                 445

Lys Ala Arg Glu Glu Leu Ser Arg Leu Gln Gln Glu Thr Ala Gln Leu
    450             455             460

Glu Glu Ser Val Glu Ser Gly Lys Ala Gln Leu Glu Pro Leu Gln Gln
465             470             475                 480

His Leu Gln Glu Ser Gln Gln Glu Ile Ser Met Gln Met Arg Leu
                485             490             495

Glu Met Lys Asp Leu Glu Thr Asp Asn Asn Gln Ser Asn Trp Ser Ser
            500             505             510

Ser Pro Gln Ser Val Leu Val Asn Gly Ala Thr Asp Tyr Cys Ser Leu
        515             520             525

Ser Thr Ser Ser Ser Glu Thr Ala Asn Phe Asn Glu His Ala Glu Gly
    530             535             540

Gln Asn Asn Leu Glu Ser Glu Pro Thr His Gln Glu Ser Ser Val Arg
545             550             555             560

Ser Ser Pro Glu Ile Ala Pro Ser Asp Val Thr Asp Glu Ser Glu Ala
            565             570             575

Val Thr Val Ala Gly Asn Glu Lys Val Thr Pro Arg Phe Asp Asp
            580             585             590

Lys His Ser Lys Glu Glu Asp Pro Phe Asn Val Glu Ser Ser Ser Leu
        595             600             605

Thr Asp Ala Val Ala Asp Thr Asn Leu Asp Phe Phe Gln Ser Asp Pro
610                 615             620

Phe Val Gly Ser Asp Pro Phe Lys Asp Asp Pro Phe Gly Lys Ile Asp
625             630             635             640

Pro Phe Gly Gly Asp Pro Phe Lys Gly Ser Asp Pro Phe Ala Ser Asp
            645             650             655

Cys Phe Phe Lys Gln Thr Ser Thr Asp Pro Phe Thr Thr Ser Ser Thr
            660             665             670

Asp Pro Phe Ser Ala Ser Ser Asn Ser Ser Asn Thr Ser Val Glu Thr
        675             680             685

Trp Lys His Asn Asp Pro Phe Ala Pro Gly Gly Thr Val Val Ala Ala
        690             695             700

Ala Ser Asp Ser Ala Thr Asp Pro Phe Ala Ser Val Phe Gly Asn Glu
705             710             715             720

Ser Phe Gly Asp Gly Phe Ala Asp Phe Ser Thr Leu Ser Lys Val Asn
            725             730             735

Asn Glu Asp Ala Phe Asn Pro Thr Ile Ser Ser Ser Thr Ser Ser Val
            740             745             750

-continued

| Thr | Ile | Ala 755 | Lys | Pro | Met | Leu | Glu 760 | Glu | Thr | Ala | Ser | Lys 765 | Ser | Glu | Asp |
| Val | Pro 770 | Pro | Ala | Leu | Pro 775 | Lys | Val | Gly | Thr | Pro 780 | Thr | Arg | Pro | Cys | |
| Pro 785 | Pro | Pro | Pro | Gly | Lys 790 | Arg | Pro | Ile | Asn | Lys 795 | Leu | Asp | Ser | Ser | Asp 800 |
| Pro | Leu | Lys | Leu | Asn 805 | Asp | Pro | Phe | Gln | Pro 810 | Phe | Pro | Gly | Asn | Asp 815 | Ser |
| Pro | Lys | Glu | Lys 820 | Asp | Pro | Asp | Met | Phe 825 | Cys | Asp | Pro | Phe | Thr 830 | Ser | Ser |
| Thr | Thr | Thr 835 | Asn | Lys | Glu | Ala | Asp 840 | Pro | Ser | Asn | Phe | Ala 845 | Asn | Phe | Ser |
| Ala | Tyr 850 | Pro | Ser | Glu | Glu | Asp 855 | Met | Ile | Glu | Trp | Ala 860 | Lys | Arg | Glu | Ser |
| Glu 865 | Arg | Glu | Glu | Glu | Gln 870 | Arg | Leu | Ala | Arg | Leu 875 | Asn | Gln | Gln | Glu | Gln 880 |
| Glu | Asp | Leu | Glu | Leu 885 | Ala | Ile | Ala | Leu | Ser 890 | Lys | Ser | Glu | Ile | Ser 895 | Glu |
| Ala | | | | | | | | | | | | | | | |